(12) United States Patent
Rosenberg

(10) Patent No.: US 7,110,792 B2
(45) Date of Patent: Sep. 19, 2006

(54) APPARATUS AND METHOD FOR INCREASED SECURITY OF WIRELESS TRANSACTIONS

(76) Inventor: Einar Rosenberg, 1801 Rosewood Way, Palm Beach Gardens, FL (US) 33418

(\*) Notice: Subject to any disclaimer, the term of this patent is extended or adjusted under 35 U.S.C. 154(b) by 0 days.

(21) Appl. No.: 10/848,405

(22) Filed: May 19, 2004

(65) Prior Publication Data

US 2004/0235450 A1 Nov. 25, 2004

Related U.S. Application Data

(60) Provisional application No. 60/471,351, filed on May 19, 2003.

(51) Int. Cl.
*H04M 1/00* (2006.01)

(52) U.S. Cl. .............. 455/558; 455/406; 455/557; 455/556.2; 379/114.19; 379/114.21; 235/380

(58) Field of Classification Search ............ 455/558, 455/557, 556.2, 575.1, 550.1, 412.1, 406; 379/114.19, 114.21, 114.23; 235/380

See application file for complete search history.

(56) References Cited

U.S. PATENT DOCUMENTS

| | | | | |
|---|---|---|---|---|
| 6,115,601 | A * | 9/2000 | Ferreira | 455/406 |
| 6,424,845 | B1 * | 7/2002 | Emmoft et al. | 455/575.1 |
| 6,801,787 | B1 * | 10/2004 | Page et al. | 455/556.1 |
| 2001/0044321 | A1 * | 11/2001 | Ausems et al. | 455/556 |
| 2002/0016186 | A1 * | 2/2002 | Chambon et al. | 455/558 |
| 2003/0083042 | A1 * | 5/2003 | Abuhamdeh | 455/406 |
| 2004/0127256 | A1 * | 7/2004 | Goldthwaite et al. | 455/558 |
| 2004/0176071 | A1 * | 9/2004 | Gehrmann et al. | 455/411 |

\* cited by examiner

*Primary Examiner*—Danh Cong
(74) *Attorney, Agent, or Firm*—Dickstein Shapiro Morin & Oshinsky LLP

(57) ABSTRACT

A mobile communication device with security mechanisms is provided for enabling wireless personal information transfer with increased security. In another embodiment of the invention, a mobile communication device is used to confirm a transaction.

31 Claims, 16 Drawing Sheets

800

APPARATUS AND METHOD FOR INCREASED SECURITY OF WIRELESS TRANSACTIONS

This application claims the benefit of U.S. Provisional Application No. 60/471,351 filed May 19, 2003, which is incorporated herein by reference in its entirety.

BACKGROUND OF INVENTION

The present invention relates to wireless electronic data transfer, and to circuits and methods for secure wireless information transactions.

A Smartcard is a plastic card with an embedded integrated circuit computer chip (i.e., a piece of thin, semiconductor material, such as silicon) that has been chemically processed and etched with a specific set of electrical characteristics such as circuits, storage, and logic elements of smartcard elements. When coupled with a Smartcard reader, this combination has the processing power to perform the complex operations previously requiring a personal computer or other large logic device.

In the form of a credit card, a Smartcard contains a built-in semi-conductor chip. The chip memory stores payment information, e.g., account information, similar to a magnetic stripe on the back of a credit card, but may also include additional information such as issuer-defined controls (e.g., online authorization frequency requirements, floor limits, credit limit, etc.). Many smartcards issued in the United States will also include an embossed sixteen-digit account number in the magnetic stripe. The non-chip features allow the smartcard to be used at storefronts that are not equipped to interact with smart chips. Smartcards can also be contactless or wireless, meaning the smartcard transfers data to and from another Smartcard enabled device via a built-in antenna without physically touching the other Smartcard enabled device.

Smartcard chips can be categorized as either intelligent chips or memory chips. Intelligent chips, i.e., smart chips, contain a microprocessor that has various read/write capabilities (e.g., EEPROM and ROM space), and the smart chip interacts with a Smartcard reader using software applications stored on the chip. Conversely, some Smartcard memory chips lack processing capability and do not manage files dynamically. Generally, the Smartcards currently issued by bank card issuers in the United States for payment contain intelligent chips and have processing power. For example, a Smartcard could contain an access control application where the smart chip authenticates the cardholder and provides the user with access to a previously locked door or computer network. Information on the smart chip is read from a Smartcard reader, and the smart chip is designed so that some of the information stored in the smart chip cannot be changed.

A smart chip operates similarly to a personal computer, e.g., it can control the execution of the applications and it can store information. A smart chip can also lack processing power—be "dumb card." The primary difference with a smart chip is that the operating system is programmed into the ROM portion of the chip at the time of the manufacture and generally cannot be altered. There exist several different smartcard operating systems. Between the operating system and the application is an application programming interface ("API")—the message management process through which the operating system and the applications interact. The operating system and breadth of applications on the smart chip are not necessarily important to the merchant and card user, as long as it is an open platform that can interface with a Smartcard reader and provide payment information to the merchant's POS terminal.

Software applications on the chip are designed for security and to process transactions. Additional applications or information may be added by the issuing bank, or potentially the card holder, such as a loyalty program, a stored value application, an e-ticket program, or a secure access verification program. When the Smartcard is used to transact payment, a point of sale ("POS") device often requires a PIN to authenticate the user. Conventional debit and ATM networks authenticate the PIN entered by the cardholder using a back-end network (e.g., the POS device contacts, directly or indirectly, the financial network of the user that corresponds to the account number stored in the smartcard. The financial network authenticates the PIN number by comparing the account number and the PIN number associated with the account number to the PIN number entered by the user) since the PIN is not stored on debit/ATM cards. Unlike an ATM transaction, in a Smartcard transaction a PIN entered by the user is authenticated by the security system resident on the chip which examines secure information stored in the chip and compares it to the entered PIN number.

According to ISO standards, a smartcard chip operates in one of two modes either in contactless mode or in contact mode. In contactless mode, a smartcard chip is enabled to send and receive wireless communications (e.g., radio signals) through a first data channel (or data channel device). In contact mode, a smartcard chip is enabled to send and receive direct contact communications (e.g., electrically coupled signals) through a second data channel. Generally, a smartcard is pre-programmed to operate in a contactless mode and contact mode in conformance with ISO standards.

For example, when using a Smartcard to purchase goods, the consumer will hand their Smartcard to a merchant and the Smartcard is inserted into a Smartcard reader. The chip contains certain contact points that line up with the Smartcard reader to transfer information. For cards that have both a magnetic stripe and the chip, the Smartcard reader may be programmed to utilize the chip technology over the magnetic stripe since the chip is more secure. If the Smartcard contains both credit and debit applications, the cardholder must first select a payment method. At this point, the smart chip and record reader communicate to determine several things, such as whether the terminal has on-line authorization capabilities, whether the card is authentic, and processing restrictions, e.g., expiration date.

The card communicates to the reader the type of risk management checks that the card issuer wants to be performed, such as the floor limit, random online processing, and a velocity check, that determines whether an on-line authorization is necessary. Next, the POS terminal requests authorization via the back-end processing network that connects to the seller's financial institution, home office, or bank (if necessary), just like magnetic stripe card. Upon approval, the Smartcard reader and the smart chip may exchange additional information such as reward points or e-coupons for the next purchase. This information is then stored on the smart chip for future use, or could be used for the current transaction.

In contactless, or wireless, Smartcard applications, information contained on the Smartcard is transferred in one direction. Information is provided to the Smartcard reader when the Smartcard is placed in close proximity to the Smartcard reader. For example, a Mobil Speedpass smartrcard is waved near a gas pump (containing a reader) to permit the user to purchase gasoline from the pump. When the Speedpass is placed near the gas pump, the user's account information is wirelessly provided to a reader in the gas pump. The account information is then used for approval of and billing of a gasoline purchase that will follow.

In some applications, information is transferred between the Smartcard and the Smartcard reader. For example commuters may use a Smartcard to pay for subway or bus transit, where fares are conventionally paid at the beginning or conclusion of the metro transit. The Smartcard stores an "electronic cash" value on the card. When entering the metro the Smartcard is placed near the smart reader on a turnstile and the reader receives payment information from the Smartcard. The user provides no additional information to the Smartcard or Smartcard reader, and does not take any further action affirming the transaction. If the Smartcard has at least a predetermined amount of electronic cash, then the smart reader provides a signal to the Smartcard indicating the metro entry point and provides a signal to the turnstile, permitting the user to enter. If there are not sufficient electronic funds, then the Smartcard reader does not provide a signal to the turnstile, and therefore the user is not permitted to enter. To exit the metro at the end of the transit, the user places the Smartcard near the Smartcard reader of a turnstile. The Smartcard reader determines the fare (by reading the entry point from the Smartcard), and deducts the fare from the value of the electronic cash stored on the card. The Smartcard reader provides a signal to the turnstile permitting the user to exit.

As described above, a contactless Smartcard can be used for information transactions (e.g., subway or bus fare transit). However, there is little to ensure that the person using the contactless Smartcard is the same person who owns the Smartcard. As Smartcards are typically pre-programmed to operate in a contactless mode, the information on a smartcard is available to be read by any device capable of reading smartcards. For example, a valid subway card or Speedpass may be used by anyone in possession of the transit card/Speedpass, respectively, even though the possessor of the transit card/Speedpass may not be the owner of the transit card/Speedpass. Therefore, it would be desirable to have a contactless system that provides an increased level of security for the information contained within the Smartcard.

BRIEF SUMMARY OF THE INVENTION

The present invention provides methods and apparatus for wireless transactions with increased security.

In an embodiment of the invention, a smartlink module is provided to be coupled to a mobile communication device for providing the mobile communication device with the ability to transmit and receive wireless Smartcard communications to other Smartcard enabled devices. Once initialized, the mobile communication device controls the smartlink module whereby the mobile communication device selectively enables the smartlink module to transmits information. The mobile communication device requires user authentication before enabling the smartlink module. The mobile communication device also authenticates the smartlink module before enabling the module In another embodiment the mobile communication device selects the information that will be provided by the smartlink. In yet another embodiment, a mobile communication device is configured to be a wireless Smartcard transceiver.

In another embodiment of the invention, a mobile communication device facilitates information transfer. Typically, a mobile communication device mediates a financial transaction, whereby the mobile communication device authenticates the user prior to providing the user's information as part of the transaction. In one aspect, the mobile communication device requests approval of a financial transaction and when the approval is received, the mobile communication device transmits the approval to seller to complete a transaction.

In another exemplary embodiment of the invention, a mobile communication device is used to confirm a transaction. In this embodiment, when a user conducts a transaction, the user's mobile communication device is used to authenticate the user and confirm that the user is interested in completing the transaction.

In another exemplary embodiment of the invention, a smartlink module is provided, which comprises a smartcard processor, where the processor includes a first data channel being adapted to wirelessly communicate data between said smartcard processor and a third party terminal and a second data channel, said second data channel device being adapted to electrically couple said smartcard processor with a mobile communication device.

In another exemplary embodiment of the invention, a transaction controller is provided that comprises a mobile user interface device and a processor that comprises a data channel being adapted to wirelessly communicate transaction data between said processor and a third party terminal and said mobile user interface device being adapted to transmit user information to said processor said processor being disposed between said mobile user interface device and said third party terminal.

In another exemplary embodiment of the invention, a mated transaction controller is provided a smartlink module having a unique identification number and a first confirmation logic circuit, a mobile communication device coupled to said smartlink module, said device having a second unique identification number and a second confirmation logic circuit and wherein before said device enables said smartlink module to provide data information to a third party circuit said first logic circuit authenticates said smartlink module and before said smartlink module provides data information to said third party circuit said second logic circuit authenticates said mobile communication device.

In another exemplary embodiment of the invention, a transaction confirmation system is provided that includes a first computer system for storing and maintaining a user's information and for approving a transaction, a second computer for facilitating a transaction being selectively coupled to said first computer to transmit transaction information and to receive a signal back from said first computer and a third party transaction device adapted to wirelessly receive user data from a transaction controller and adapted to provide said user data to said second computer.

In another exemplary embodiment of the invention, a method of authorizing a data transaction is provided that includes the steps of receiving a user input from a user at a mobile user interface device; validating an identity of said user within mobile user interface device to produce a validation signal; producing a validation signal based on said validating; receiving said validation signal at an input port of a smartcard processor; and transmitting user personal data from smartcard processor.

BRIEF DESCRIPTION OF THE DRAWINGS

These and other features and advantages of the invention will be more readily understood from the following detailed description of the invention which is provided in connection with the accompanying drawings, in which.

DETAILED DESCRIPTION OF THE INVENTION

In the following detailed description, reference is made to the accompanying drawings, which form a part hereof, and in which is shown by way of illustration specific embodiments in which the invention may be practiced. These embodiments are described in sufficient detail to enable those of ordinary skill in the art to make and use the invention, and it is to be understood that structural, logical, or procedural changes may be made to the specific embodiments disclosed without departing from the spirit and scope of the present invention.

Although not intended to be limiting, a "smartlink" system in a preferred embodiment is a system that includes a smartlink server and smartlink capable device. A smartlink server is a computer or processing system that maintains information about users of smartlink capable devices. This information may include a user's account information, device information, and the like. The smartlink server is capable of communicating with a user's smartlink capable device through cellular communications as is conventionally known. The smartlink server is capable of communicating with other computer servers (of seller's, banks, and other institutions) through conventional means. A smartlink capable device can be any such embodiment or aspect of the invention described below.

Figure 1:
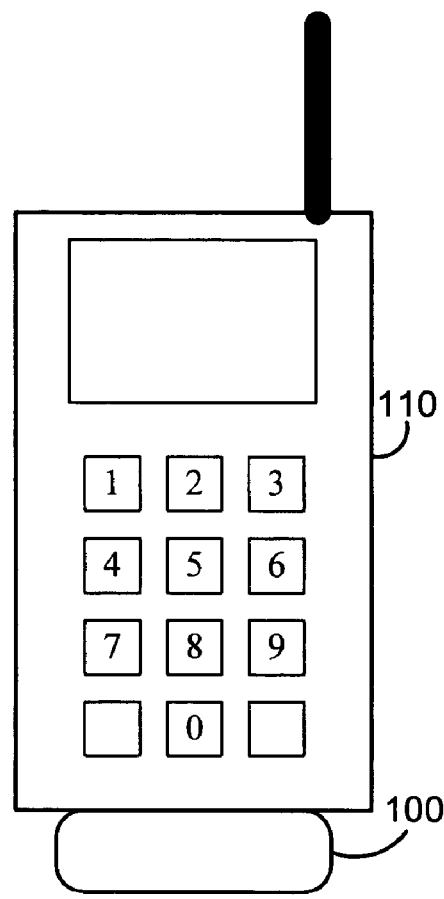
FIG. 1 shows the smartlink coupled with a mobile communication device in accordance with an exemplary embodiment of the invention.

FIG. 1 shows a smartlink module 100 coupled to mobile communication device 110, e.g., a cell phone, in accordance with an exemplary embodiment of the invention. The mobile communication device 110 controls and exchanges information with the smartlink module 100, which is explained in greater detail below. In a preferred embodiment, the mobile communication device 110 has a processing unit using a Java J2ME engine. Although described with reference to a the mobile communication device 110 having a Java J2ME engine, the invention is not intended on being so limited.

Figure 2:
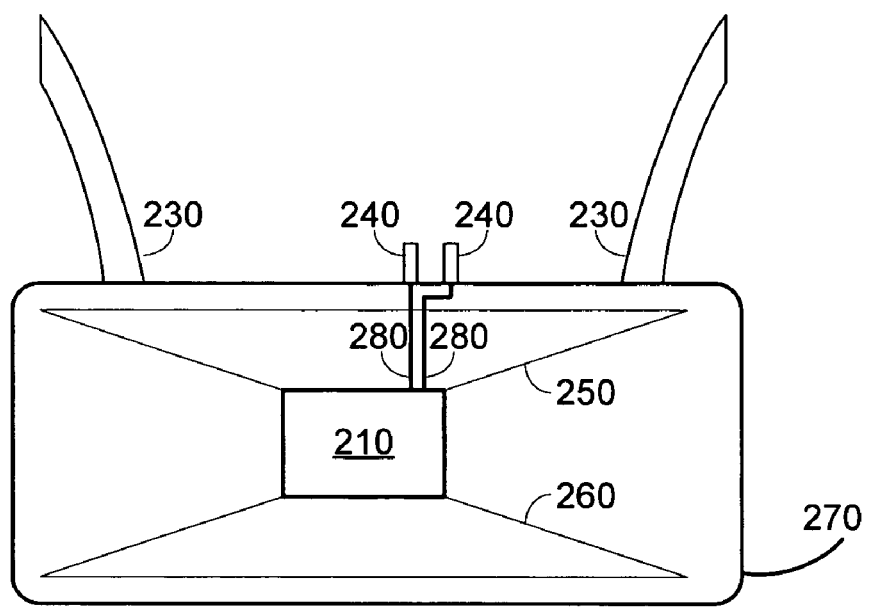
FIG. 2 is a cut away, front view of the smartlink of FIG. 1 in accordance with an exemplary embodiment of the invention.

FIG. 2 is a front-side, cut away view of a smartlink module 100 in accordance with an exemplary embodiment of the present invention. Smartlink module 100 includes processing chip 210 and antennas 250, 260. Smartlink module 100 also includes communication connection pins 240 and mounting clips 230.

The processing chip 210—e.g., smartchip—provides processing and memory storage including, but not limited to data conversion processing. One feature of processing chip 210 is that it converts data between radio waves and digital/analog signals. Typically, communication between contactless Smartcard devices utilizes radio waves in the form of digital packets. In a preferred embodiment, processing chip 210 converts data received in the form of radio waves by one of the antennae 250, 260 to data in the form of digital/analog signals that are then provided to the mobile communication device 110 (FIG. 2) through communication path 280 and connection pin 240. Further, the processing chip 210 converts from data in the form of digital/analog signals that are received from the mobile communication device 110 through communication path 280 and connection pin 240 to the form of radio waves provided to the antennae that will be transmitted by one of the antennae 250, 260. It is known with those with skill in the art how a processing chip 210 converts data between the form of radio waves and the form of the digital/analog signals utilized by a mobile communication device 110, or other device incorporating a smartcard transceiver. For example, a mobile communication device 110 through the smartlink module 100 (FIG. 1) can exchange information with a POS device (not shown) having a smartcard reader/writer, e.g., a smartcard transceiver. In a preferred embodiment, the processing chip 210 is similar to a smartcard chip in a conventional smartcard that conforms with ISO standards. Although generally described with processing chip 210 performing processing steps, the invention is not intended to be so limited. Processing may also be performed, for example, by a mobile communication device 110 coupled to the processing chip 210 or by a server.

The processing chip 210 is preferably preprogrammed with an initialization program, which is described more fully below. Further, the processing chip 210 in each smartlink module 100 is pre-programmed with a unique identification code, which is coded on each processing chip 210. In a preferred embodiment, the hard coding of the identification code occurs during manufacture. In other aspects, the hard coding of the identification code occurs after the manufacture of the chip.

Antennas 250, 260 provide wireless communication with another device capable of sending and/or receiving Smartcard signals. In a preferred embodiment, one of antennas 250, 260 is used for very short range communications, where the distance between the antennae 250, 260 and an other smartcard transmitter/receiver, e.g., a POS unit contactless module, is only a few inches. The other of the antennae 250, 260 is used for longer range communications, where the distance between the antennae 250, 260 and the other transmitter/receiver is several feet. In a preferred embodiment, a smartlink module 100 will use conventional contactless Smartcard radio frequencies as established by ISO standards—125 kHz, and 13.56 Mhz for respectively transmitting to and receiving signals from other contactless Smartcard devices. Although the invention is described with a number of antennae used in particular manner and utilizing certain frequencies, the invention is not intended to be so limited; it is anticipated that any antenna configuration at any frequency can be employed.

Communication connection pins 240 provide electronic coupling between the smartlink module 100 and a mobile communication device. The communication connection pins 240 are adapted to couple with communication pins or the port of a mobile communication device 110. The number and location of communication connection pins 240 is dependent on the particular mobile communication device 110 that the smartlink module 100 is intended on being coupled with. The communication connection pins 240 are electronically coupled to the chip 210 by communication paths 280, respectively. Although shown with two communication paths 280, the number of communication paths 280 can vary.

Mounting clips 230 provide physical coupling between the smartlink module 100 and a mobile communication device (as seen in FIG. 2). The number and location of mounting clips 230 is dependent on the particular mobile communication device that the smartlink module 100 is intended on being coupled to. Although described as "clips," the invention is not intended to be so limited and may incorporate any appropriate method of fastening that couples the smartlink module 100 to a mobile communication device 110.

The housing 270 of a smartlink module 100 in a preferred embodiment is one inch wide by one quarter of an inch tall by one quarter of an inch deep. However, the actual dimensions of the housing 270 can vary. The housing can be constructed of various materials, however, in a preferred embodiment; the housing is constructed from plastic. When a user requests a smartlink module 100 for use with the user's mobile communication device 110, the user indicates the make and model of the user's mobile communication device 110 to a smartlink module provider (e.g., a supplier, retailer, wholesaler, financial institution). The user is provided with a smartlink module 100 with a housing 270 adapted to the particular make and model of mobile communication device 110. Further, the number and location of communication connection pins 240, the connection clips 230, and communication paths 280 is dependant to the mobile communication device 110. In another aspect, the smartlink module 100 is universally adaptable.

In one aspect of the invention, the mobile communication device 110 controls the operation of the processing chip 210. The mobile communication device 110 provides a signal to the processing chip 210 indicating that the processing chip 210 should be operating in either contactless or contact mode. In contactless mode, the processing chip 210 is enabled to send and/or receive wireless signals. In contact mode, the processing chip 210 is enabled to send and/or receive direct electrically coupled signals. In a preferred embodiment, a mobile communication device 110 controls the processing chip 210 through the use of an application program that resides on the mobile communication device 110. For example, after the mobile communication device 110 is initialized (as described below) a Secure transfer program resides on the mobile communication device 110. The Secure transfer program resides as an executing process in the background of programs executing on the mobile communication device 110 as a background process until activated for a transaction process, at which time, the Secure transfer program resides in the foreground. When a transaction process is completed, the Secure transfer program again resides as a background process.

To use the smartlink module 100 with a mobile communication device 110 requires that the smartlink module 100 and mobile communication device 110 combination first be initialized. When the smartlink module 100 is preferably provided to a user an initialization program resides in the chip 210 (FIG. 2). Alternatively, for example, a user can download the initialization program through the mobile communication device 110 via the cellular link by dialing a designated telephone number and then receiving an initialization application downloaded to the mobile communication device. Alternatively, a user may link a mobile communication device 110 to another source that provides access to an initialization application.

Initialization occurs a first time that a smartlink module 100 is coupled to the mobile communication device 110 and the mobile communication device 110 is subsequently activated. For example, when the smartlink module 100 is first coupled and the mobile communication device 110 is activated, an initialization program within the processing chip 210 of the smartlink module 100 is activated. The initialization program provides the processor of the mobile communication device 110 with an application from the smartlink module 100 that generally includes two pieces of information: the address of the location from which to download information, e.g., a phone number to call a link or server connected to a location, and information on how to access a cellularly connected or internet connected server located at a unique mobile IP address.

The second piece of information is the unique identification of the smartlink module 100, and possibly, the user's financial transaction identification, e.g., a bank account number or credit card number of the user. The initialization program on the mobile communication device 110 initiates a call to the user's financial institution/transaction company, e.g., the bank or credit card company that issued the smartlink module 100 or an institution that will be financially responsible for payments. The mobile communication device 110 provides the bank the two pieces of information as well as the unique identification of the mobile communication device 110, e.g., the Electronic serial number. The mobile communication device 110 receives from the bank several pieces of data including, for example, the user's name, address, phone, and other information about the user, which are stored in the mobile communication device 110. The bank also provides to the mobile communication device 110 an application, e.g., a secure transfer program that resides in the mobile communication device 110 and enables the use of the smartlink module 100 with the mobile communication device 110 as described in greater detail below.

The initialization program running on the mobile communication device 110 prompts the user for a PIN number that is stored within the mobile communication device 110. The PIN number may also be provided to the bank and also stored at the bank. The PIN number is, for example, a series of at least four alphanumeric characters. The PIN number helps prevent undesirable access to the user's information stored in the mobile communication device 110. In another aspect, the initialization continues to enable additional features. A user's PIN information (e.g., password) is different from said user's personal information (e.g., financial account information, credit card).

During initialization of the smartlink module 100 and mobile communication device 110, identifying information of the mobile communication device 110, e.g., the ESN or manufacturer serial number is stored in the smartlink module 100. The identifying information of the mobile communication device can be supplied in many ways, including, for instance from the financial institution, from the user during initial application for a smartlink or subsequently when accessed by the application. Also during initialization, identifying information of the smartlink module 100, e.g. The smartlink module 100 identification code, is stored in the mobile communication device 110. In a preferred embodiment, this identifying information stored in the mobile communication device 110 and smartlink module 100 cannot be deleted or modified after it is first stored.

The mobile communication device 110 also requires an application program for a mobile communications device 110 to operate the smartlink module 100. In a preferred embodiment, an application program is loaded into the mobile communication device 100 through a cellular connection and then stored within the mobile communication device. For example, during initialization, a Secure transfer program is downloaded into the mobile communication device 110. Preferably, after the Secure transfer program is downloaded to the mobile communication device 110, the program begins execution as a back ground.

After the initialization successfully occurs and during subsequent use of the mobile communication device, the smartlink module 100 is "mated" to the mobile communication device 110. A program in the smartlink module 100 compares the identifying information of the mobile communication device 110 currently coupled to the smartlink module 100 to the stored identifying information of the mobile communication device 110. The smartlink module 100 is enabled to send and receive signals only if the current mobile communication device 110 identifying information corresponds to the stored mobile communication device 110 identifying information. Similarly, during subsequent use of the mobile communication device 110, a Secure transfer program in the mobile communication device 110 compares the identifying information of the smartlink module 100 currently coupled to the mobile communication device 110 to the stored identifying information of the smartlink module 100. The mobile communication device 110 is enabled to send and receive signals to the smartlink module 100 only if the current smartlink module 100 identifying information corresponds to the stored smartlink module 100 identifying information. In a preferred embodiment, the respective programs that compare the identification numbers are part of the circuitry of the smartlink module 100 and mobile communication device 110, respectively.

Figure 3:
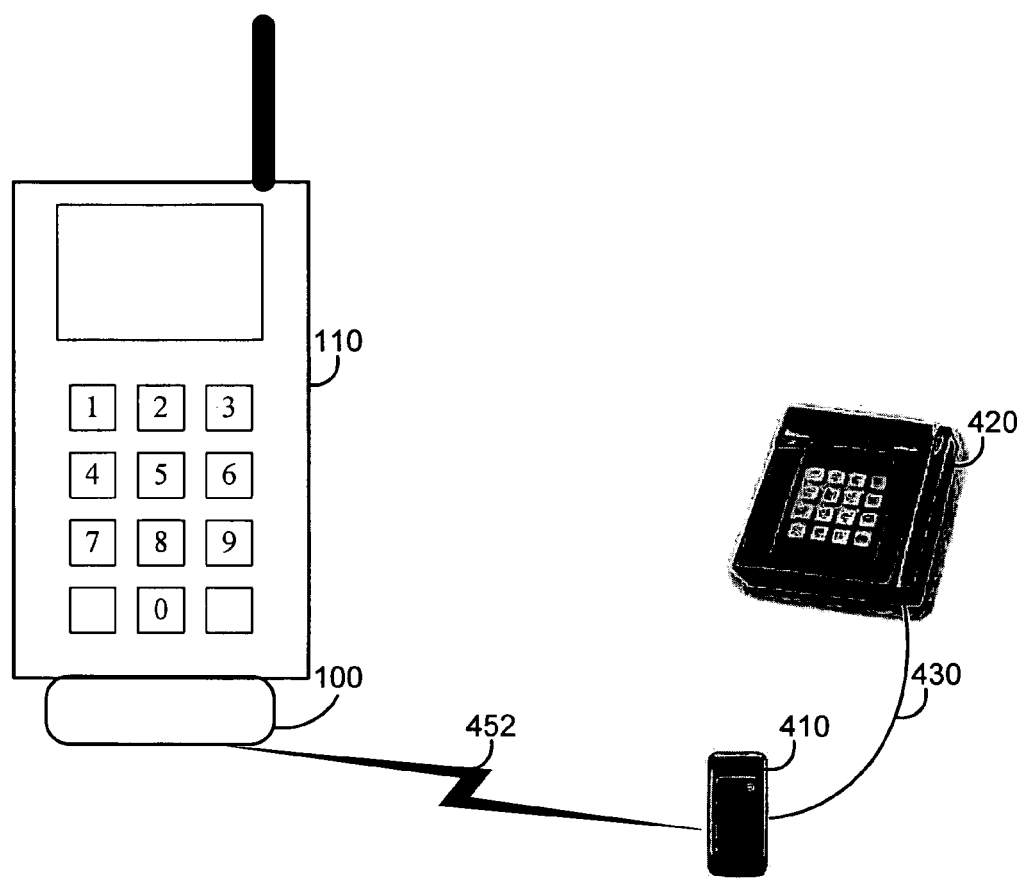
FIG. 3 shows the smartlink and mobile communication device of FIGS. 1 and 2 used in a transaction.

FIG. 3 depicts the use of an exemplary embodiment of the invention where a smartlink module 100 coupled with a mobile communication device 110 provides information to a POS device 420 through a smartcard reader 410. In this use, the mobile communication device 110 selectively enables the smartlink module 100 for contactless information transfer. When the smartlink module 100 is enabled, information stored in the smartlink module 100, e.g., a user's account information, is provided in the form of radio waves that can be read by a smartcard reader. The mobile communication device 110 enables the smartlink module 100 to operate in contactless mode after the secure transfer program has received the appropriate PIN number and authenticates that the user is the owner of the mobile communication device 110. Otherwise, the mobile communication device 110 enables the smartlink module 100 to operate in wired mode thereby disabling wireless mode.

As seen in FIG. 3 a smartlink module 100 is coupled to a mobile communication device 110. A POS transaction device 420, e.g., a credit card reader or a cash register, is coupled to a Smartcard enabled radio transmitter/receiver device 410, e.g., a contactless Smartcard receiver/transmitter. The device 410 provides communication between the smartlink module 100 of the mobile communication device 110 and the POS transaction device 420. The POS transaction device 420 provides data to the radio device 410; the radio device 410 provides the data in the form of radio transmissions 452 to the smartlink module 100. The smartlink module 100 provides radio transmissions 452 to the radio device 410; the transmissions received by the radio device 410 are converted by the radio device 410 into a form recognizable by the POS device 420 and provided to the POS device 420.

Figure 4:
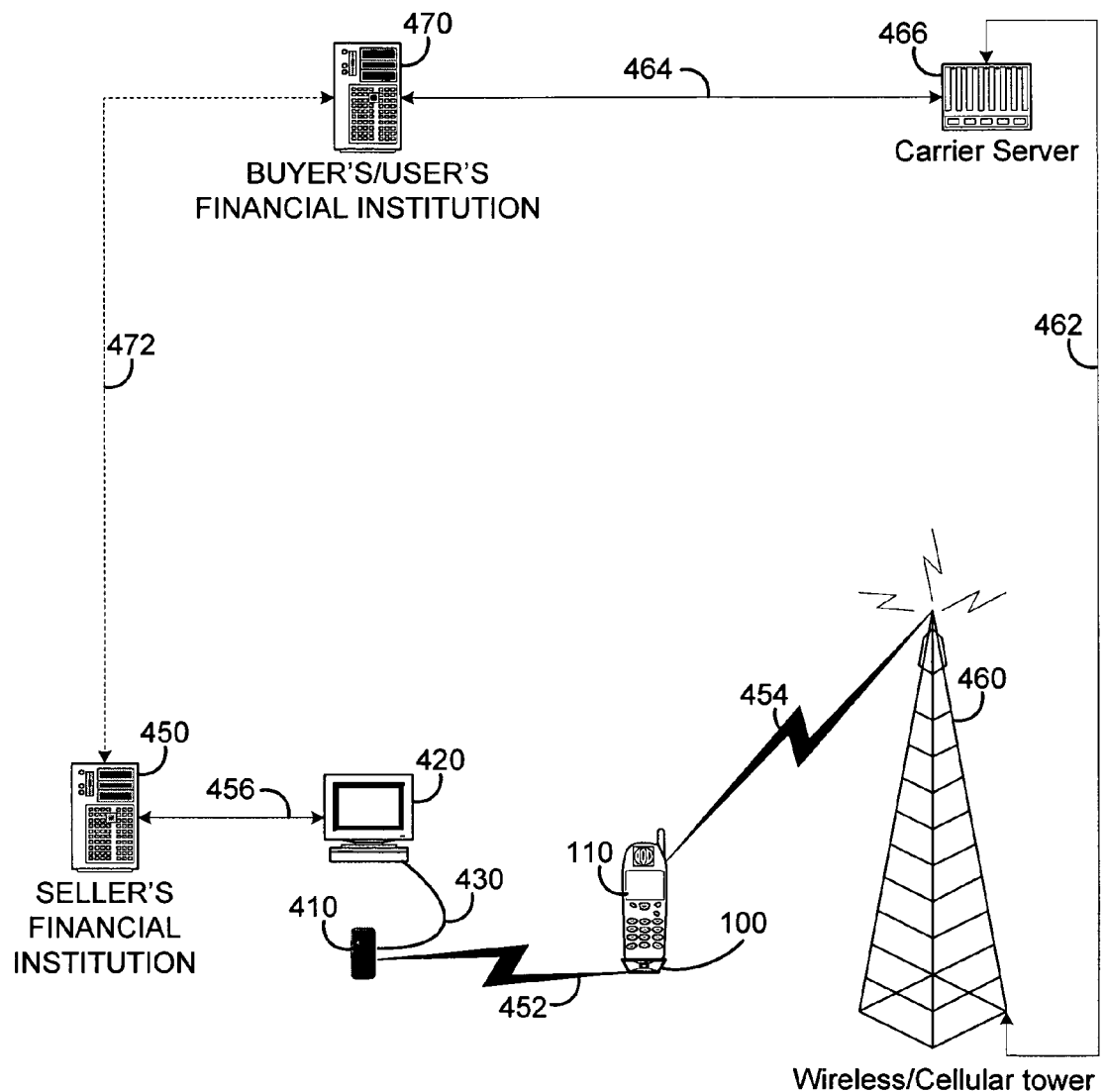
FIG. 4 shows the smartlink and mobile communication device of FIG. 3 used in a transaction in greater detail.

FIG. 4 depicts an exemplary use of the invention 100 in greater detail. As seen in FIG. 4, it is known that a seller's POS device 420 is adapted to be selectively coupled to the seller's financial institution server 450 through line 456, typically a telecommunication cable. Further, it is known that a mobile communication device 110 is adapted to be coupled to a wireless communication tower(s) 460 through wireless transmissions 454, which is connected to the user's wireless carrier server 466 through line 462, typically a telecommunication cable. Further, it is known to be able to connect a user's wireless carrier server 466 to the user's financial institution server 470 through line 464. It is also conventionally known that a user's/buyer's financial institution server 470 and seller's financial institution server 450 can communicate with each other to exchange information. In a conventional use of smartcard processing chip communications, information is transferred between a smartcard transmitter and a smartcard receiver in buckets of data, which is known to those with skill in the art.

Figure 5:
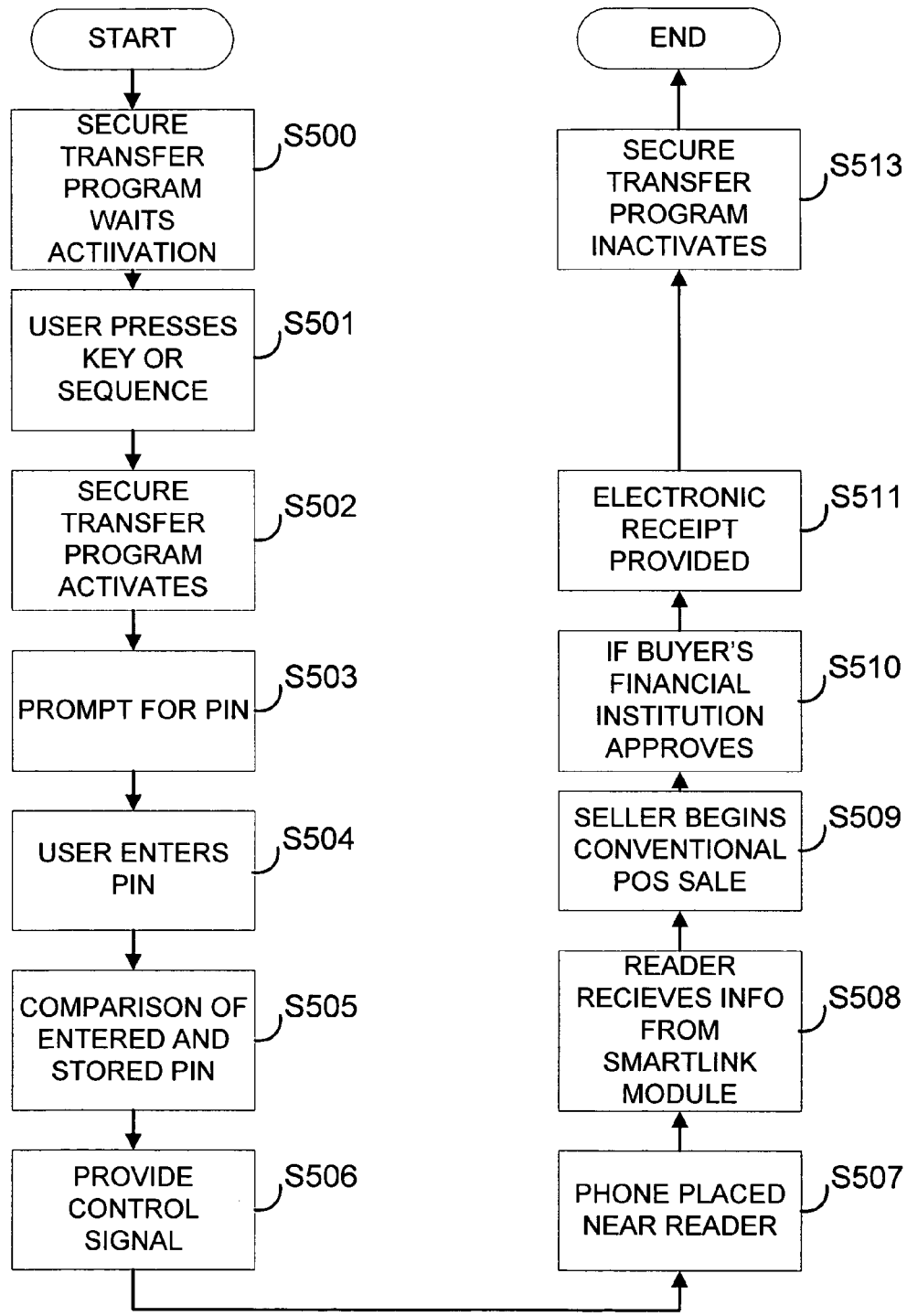
FIG. 5 shows a flow chart depicting the operation of the devices of FIGS. 1–4 according to an exemplary embodiment of the invention.

FIG. 5 depicts a flow chart indicating the method of use of an exemplary embodiment of the invention applied in the context of a point of sale ("POS") transaction. Once the mobile communication device 110 has been initialized for use with the smartlink module 100, a secure transfer program resides in the mobile communication device 110. When the mobile communication device 110 is activated, the secure transfer program runs in the background of the mobile communication device 110 processes. When the program is running in the background it is transparent to the user. The secure transfer program runs in a "passive" mode and waits for an activation signal. The activation signal is, for example, a signal from the mobile communication device, for example, by the user entering a key sequence (e.g., one or more keys or buttons being pressed) on the mobile communication device. When the Secure transfer program receives the activation signal the program becomes active and runs as a foreground processes.

In the following process 500, the operation of the processing chip 210 converting data from/to radio waves to digital/analog electrical signals takes place in the background of process 500, although no specific process segment is specifically mentioned. (as show in FIG. 5):

In segment S500, the secure transfer program waits for a signal from a mobile communication device by the user. It is assumed that before the process begins, the secure transfer program is running as a process in the mobile communication device 110. The precursor steps to segment S500 are that the user begins to purchase goods in a conventional manner. The goods are processed by the sales person at their register. When the processing of goods is complete, e.g., all the goods have been scanned, the items are totaled. The sales person then prompts the user for the method of payment. The process continues to segment S501.

In segment S501, the user performs a key sequence on a mobile communication device 110 coupled with the smartlink module 100 appropriate to activate the smart transfer program. Process continues to segment S502.

In segment S502, the secure transfer program recognizes the key sequence and the secure transfer program become active and executes as a foreground process in the mobile communication device. Process continues to segment S503.

In segment S503, the secure transfer program prompts the user for his PIN number. The process continues to segment S504. When the user enters his PIN number. The process continues to segment S505.

In segment S505, the secure transfer program compares the PIN number entered against the PIN number stored in the mobile communication device. If the comparison indicates that the PIN number matches, then process proceeds to segment S506.

In segment S506, the secure transfer program of the mobile communication device 110 provides a control signal to the coupled smartlink module 100 to enable contactless mode. With the smartlink module 100 in contactless mode, the smartlink module is enabled to transmit, e.g., provide information, stored in the smartlink module 100. The process continues to segment S507.

In segment S507, the user places the mobile communication device 100 near the seller's smartcard reader 4110 associated with the seller's POS device 420. The process continues to segment S508.

In segment S508, the seller's smartcard reader 410 receives information transmitted from the user's smartlink module 100. The process continues to segment S509.

In segment S509, using the information received from the smartlink module 100, the seller's device 410 provides that information to the seller's financial institution server 450 (FIG. 4) and traditional processing POS transaction processing begins (as is conventionally known). The process continues to segment S510.

In segment S510, the system tests whether the transaction has been approved by the buyer's financial institution server 470 (FIG. 4). The process continues to segment S511.

In segment S511, in another aspect of the invention, the buyer's and/or seller's financial institution server 470/450 provides an electronic receipt to the user's mobile communication device 110. The receipt is preferably provided in the form of a digital communication (e.g., SMS) that is stored in the mobile communication device 110. In yet another aspect of the invention, the user can pre-define the option where a digital receipt is sent via email to an email account of the user, with the possibility of automatically synchronizing the information with any standard accounting software. In another aspect of this embodiment, the seller's financial institution server 450 communicates with the user's financial institution server 470, and the user's financial institution server 470 (FIG. 4) sends an SMS to the mobile communication device 110. The process then continues to segment S512.

In segment S512, the purchase is completed and the process continues to segment S513.

In segment S513, the transaction is identified by the system as being complete and the secure transfer program stops running as a process in the foreground of processes in the mobile communication device 100 and begins running as a background process. The secure transfer program awaits another signal indicating the start of another transaction. In another aspect f the invention, the secure transfer program ceases execution.

Thus, information stored in the smartlink module 100 is maintained more securely as the module is only in contactless mode for a short amount of time, thereby minimizing the amount of time that a smartcard reader other than the intended reader can potentially access the information stored on the smartlink module. Further, the smartlink module 100 is in contactless mode only after a user has provided a correct password.

In another aspect of the invention, the processing chip 210 and/or one or both antennae 250, 260 of the smartlink module 100 are located partially or fully within the housing of a mobile communication device and additionally may not be housed in a housing 270 (FIG. 1). In another aspect, one or both antennae 250, 260 are omitted and the smartlink module 100 utilizes either of the antennae of coupled mobile communication device 110 or a different antennae connected to the processing chip 210. In yet another aspect, a processing chip 210 is incorporated as part of the circuitry of a mobile communication device 110 or the processing chip 210 may be separate but connected to the mobile communication device 110 for communications purposes. In still another aspect of this embodiment of the invention, the smartlink device is coupled to a mobile communication device 110 port, where the port permits communication with the mobile communication device 110. Further, the port is at least partially within the housing of the mobile communication device 110. For example, the port is a "spring board" in a Handspring device.

In another aspect of this embodiment, the processing chip 210 is disposed in a non-cellular communication device ("NCC device"), i.e., device that does not have a cellular connection. In this aspect of the invention, the NCC device operates differently from the operation of the exemplary embodiment of the invention described with reference to FIGS. 4,5 in that in this aspect, the secure transfer program does not receive a transaction confirmation signal from the user's or seller's bank. The NCC device provides financial transaction information to the POS device 420 through Smartcard reader 410, and the POS device 420 initiates the conventional back-end processing of financial transactions. The POS device may provide a transaction confirmation signal to the NCC device when the transaction is successful. The operation of the confirmation process would be similar to that as described with reference to FIG. 5, however, the NCC device would not receive a signal (e.g., an SMS signal) providing a receipt for the transaction (Segment S511).

Figure 6:
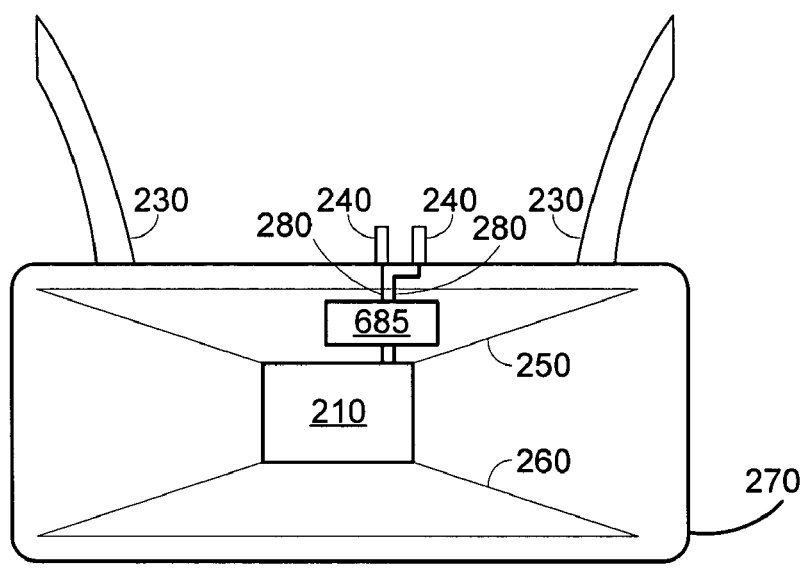
FIG. 6 shows a smartlink module in accordance with another exemplary embodiment of the invention.

FIG. 6 depicts a cut away view of a smartlink module in accordance with another exemplary embodiment of the invention. As seen in FIG. 6, similar to smartlink 100, smartlink module 600 includes processing chip 210, antennas 250, 260, communication connection pins 240 and mounting clips 230 in a housing 270.

Smartlink module 600 includes a translation circuit 685. Translation circuit 685 facilitates communication between a mobile communication device 110 and processor chip 210. In a preferred embodiment, the translation circuit 685 is a core logic circuit Although off-the-shelf core circuit can be used, ASICs can also be utilized. With the use of the translation circuit 685, the mobile communication device 100 can write data to and read data from the smartlink module 600. In the embodiment of the invention described above, a user's personal data is stored in the smartlink module 100. In this embodiment of the invention, the secure transfer program of the mobile communication device 110 provides data to the smartlink module 600. The secure transfer program of the mobile communication device 110 reads data from the smartlink module 600. In a preferable use of this embodiment, the mobile communication device 110 provides a user's personal information to the smartlink module 600 shortly before it is needed for use, i.e., before the smartlink module 600 provides the information. Preferably, shortly after the personal information is provided, the information is removed, e.g., deleted, from the smartlink module. Since a user's personal information is only temporarily stored in the smartlink module 600, the user's personal information is more securely stored by remaining most of the time only in the mobile communication device 110. Additionally, since a user's data is only temporarily maintained in the smartlink module 600, the need to securely maintain the smartlink module 600 is decreased. Therefore, the smartlink module 600 need not always have its contactless mode be disabled to provide additional safeguards for a user's information.

Additionally, since the secure transfer program can write selected information to the smartlink module 600, the secure transfer program and/or the user can choose what information is provided to the smartlink module 600. For example, for a financial transaction, a user may have several different financial accounts that he has stored information in the mobile communication device 110. Therefore, when making a purchase, he may choose which financial account he would prefer to make his payment with, e.g., American Express or VISA. Additionally, in the initialization process, which is similar to that described above with reference to a previous embodiment of the invention, the smartlink module 600 is not coded with a user's account information.

As part of the operation of the mobile communication device coupled with the smartlink module 600, the processing chip 600 is in conformance with the ISO standards which does not permit a Smartcard chip to operate in both contactless mode and contact mode at the same time. Consequently, to transfer information from the mobile communication device to the smartlink module 600, when the smartlink module 600 is in contact mode, the secure transfer program provides information to the smartlink module 600. After the secure transfer program provides a signal to the smartlink module 600 enabling the smartlink module 600 to operate in contactless mode, the information recently provided by the secure transfer program is able to be read by a third party smartcard reader (if within appropriate proximity.)

Figure 7:
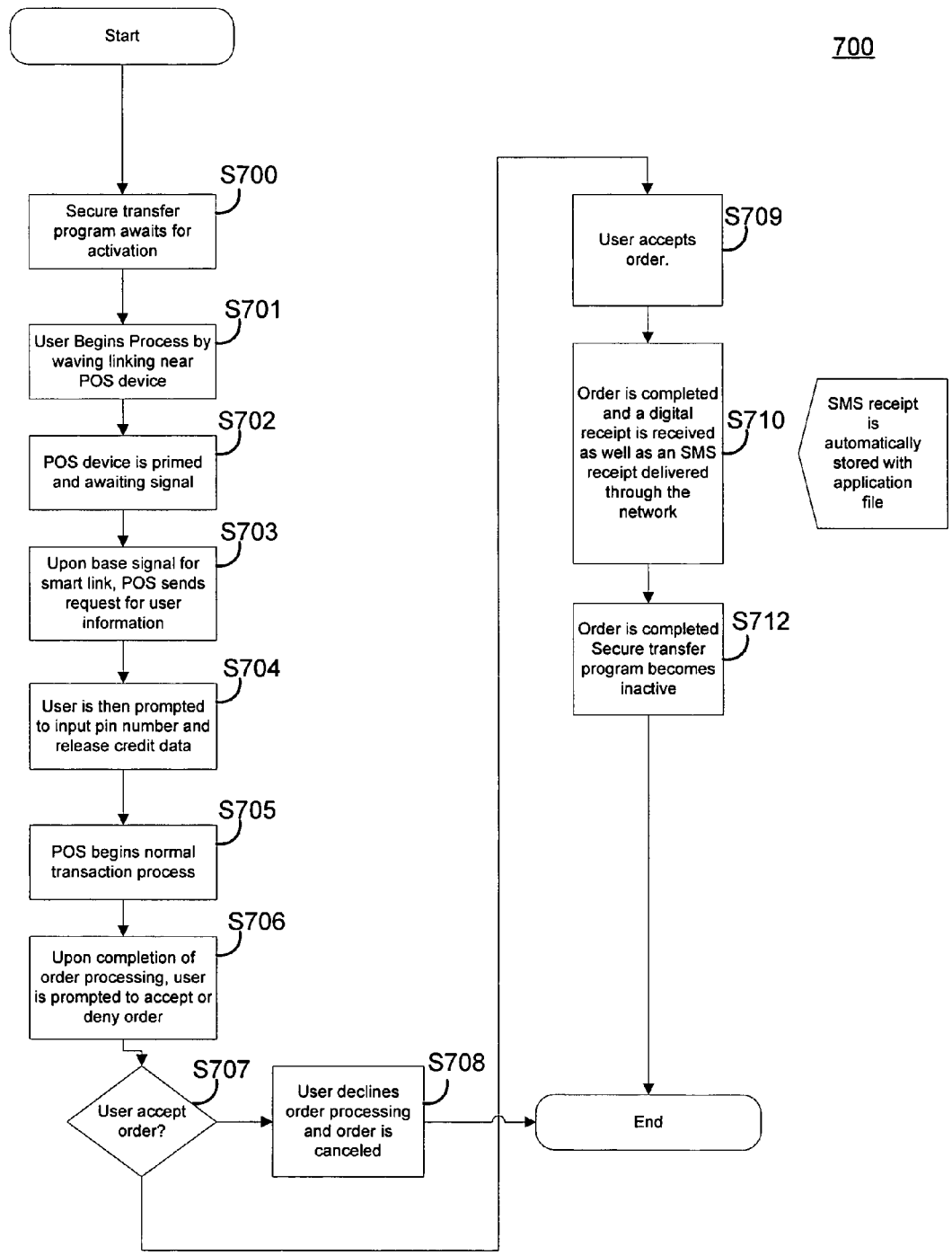
FIG. 7 shows a flow chart depicting the operation of the device of FIG. 6 according to an exemplary embodiment of the invention.

FIG. 7 illustrates an exemplary embodiment of the operation of the invention in a point of sale transaction. Once the mobile communication device 110 has been initialized for use with the smartlink module 600, a secure transfer program resides on the mobile communication device 110. When the mobile communication device 110 is activated, the secure transfer program runs in the background of the mobile communication device 110 processes. When the program is running in the background it is transparent to the user. The secure transfer program runs in a "passive" mode and waits for an activation signal. After receiving a signal from a device 410 the smartlink module 600 provides a signal to the secure transfer program indicating that a smartcard device is seeking to initiate communications. Alternatively, the secure transfer program may receive an activation signal from the mobile communication device (e.g., by the user entering a key sequent on the mobile communication device). When the secure transfer program receives the appropriate signal the secure transfer program becomes active and runs in mobile communication device 110 as the foreground processes.

In segment S700, the secure transfer program awaits a signal from a device 410 or from the mobile communication device as initiated by the user. The precursor steps are that the customer begins to purchase goods in a conventional manner. The goods are processed by the sales person at their register. When the processing of goods is complete, e.g., all the goods have been scanned, the items are totaled. The sales person then prompts the user for the method of payment. The process continues to segment S701.

In segment S701, the mobile communication device 110 with the coupled smartlink module 600 is placed near the device 410. The device 410 transmits a signal that can be received and recognized by the mobile communication device 110 and smartlink module 600 combination. The transmitted signal may be, for example, the total purchase price of the goods. The process continues to segment S702.

In segment S702, the secure transfer program awaits a signal from the device 410. When a signal is received from the device 410, then the process continues to segment S703.

In segment S703, the secure transfer program recognizes the signal from the device 410 and sends a handshaking signal back to the device 410. The device 410 then sends a signal to the secure transfer program for additional information. For example, the signal may indicate the purchase price and then the mobile communication device 110 displays the purchase price of the goods. The secure transfer program then prompts the user to see if the user agrees with the purchase price. The process continues to segment S704. Alternatively, in some cases, all the POS can do is simply send a command to the smartlink to give it information and that it is a proper and certified POS and then receive the encrypted or unencrypted information.

In segment S704, the secure transfer program requests additional information from the user. If the user agrees to the purchase price as displayed by the register of the seller, the secure transfer program requests the user input her/his unique PIN number. If the user agrees and enters the appropriate PIN number, then the secure transfer program extracts the secure financial data information, e.g., the credit card number and associated transaction information that is stored in the mobile communication device 110 or on the smartlink module 600. In either process, the mobile communication device 110 can prevent the smartlink module 600 from communicating or sending information. The secure transfer program accesses the user's information and provides it to the processing chip 210 of the smartlink module 600. The secure transfer program enables contactless operating mode and the processing chip 210 converts that information received from the secure transfer program into a radio frequency and transmits it through its associated antennae (one of 250, 260). The user's secure financial data information stored in the mobile communication device 110 is not provided without a valid PIN number. The mobile communication device 110 and smartlink module 600 provide the user's secure financial data information to the device 410. The process continues to segment S705.

In segment S705, data is received from the mobile communication device 110 and smartlink module 600 by the device 410. The device 410 provides the user's financial data information to the POS device 420 and the transaction approval continues in a conventional manner. The process continues to segment S706.

In segment S706, if the transaction has been approved by the seller's financial institution, the POS system sends a signal to the smartlink module 600 requesting confirmation. The smartlink module 600 receives the signal from the POS system, converts it from a radio signal to a digital signal, and provides that signal to the mobile communication device 110. Assuming that the secure transfer program received the converted signal, the user is then requested to confirm the amount of purchase in the user interface of the mobile communication device 110. In an other aspect of the invention, the user taps the mobile communication device and that completes the process. The process continues to segment S707.

In segment S707, the user is prompted to agree and confirm the purchase on mobile communication device 110. If the user agrees, then the process continues to segment S709. If the user does not agree, the process continues to segment S708.

In segment S708 the user has declined the purchase, and the order is cancelled. The process continues to segment S712.

In segment S709, the user has accepted the purchase. The process continues to segment S710.

In segment S710, the secure transfer program receives a digital receipt from device 410 that is stored in the mobile communication device 110. In another aspect, the seller's financial institution sends an SMS to the mobile communication device 110 providing a digital receipt. In yet another aspect, the user receives a paper receipt from the sales person. Alternatively, the user can pre-define the option where a digital receipt is sent via email to an email account of the user, with the possibility of automatically synchronizing the information with any standard accounting software. In another aspect of this embodiment, the seller's financial institution server 450 communicates with the user's financial institution server 470, and the user's financial institution server 470 sends an SMS to the mobile communication device 110. The financial institution or credit card company or some other third party, whoever is doing the transaction in the back end, and/or the seller, has the ability to send a confirmation message, generally in the form of a digital receipt.

In segment S712, the transaction is complete and the secure transfer program becomes a passive background process. Alternatively, the secure transfer program shuts off and waits for the user to activate the smartlink via the mobile communication device to begin communications with the reader.

Thus, at the end of the exemplary process 700 depicted in FIG. 7, a user has more securely provided his personal information needed for a financial transaction by only having the information stored in the smartlink module for a short period of time, thereby minimizing the amount of time that a smartcard reader other than the intended reader can access the information stored on the smartlink module. Although the inventions above are generally described with respect to financial transactions, the invention is not intended to be so limited and can be used to increase the security of any type of data that can be stored in a mobile communication device.

In another embodiment of the invention, a processing chip 210 (as shown in FIG. 6), and antennae 250, 260 of a smartlink are located within the housing of a mobile communication device. In this enablement, the antennae of the smartlink may be fully or partially within the housing of the mobile communication device. The antennae of the smartlink module 600 may also be the antennae of the phone or different antennae connected to the processing chip 210. This embodiment differs from the prior embodiment in that the chipset of the smartlink module 600 is incorporated as part of the circuitry of the mobile communication device or is separate but connected to the mobile communication device for communications purposes. For example, the chipset is coupled to the mobile communication device circuit board. Further, an antenna of the smartlink is coupled to the mobile communication device circuit board and is used for the smartlink transactions. In another aspect of this embodiment of the invention, the smartlink device is coupled to a mobile communication device port, where the port permits communication with the mobile communication device. Further, the port is at least partially within the housing of the mobile communication device. For example, the port is the spring board in a Handspring device.

Figure 8:
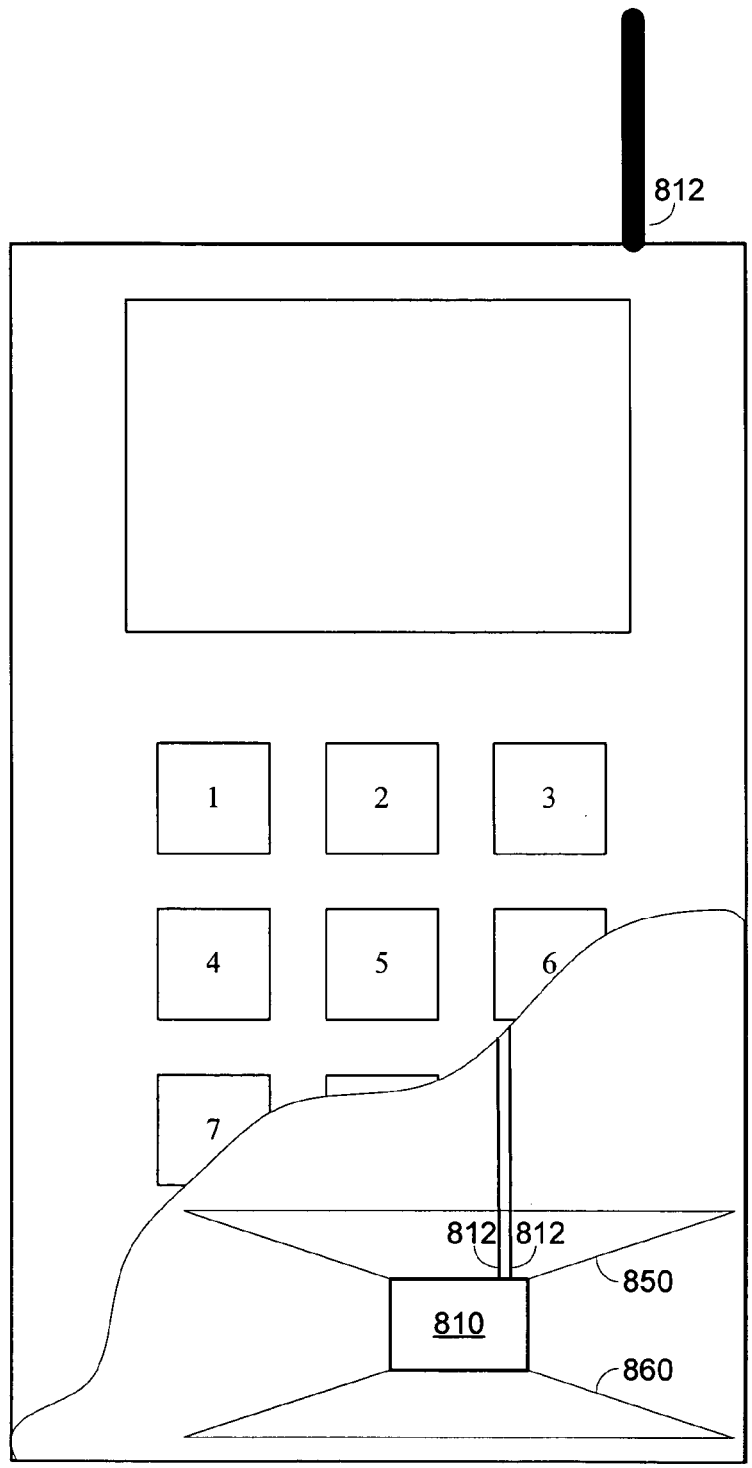
FIG. 8 shows a cutaway view of a mobile communication device in accordance with yet another exemplary embodiment of the invention.

In another embodiment of the invention, a mobile communication device 800 performs the functionality of a smartlink module (as described above in reference to either smartlink module 100 or 600), whereby the mobile communication device 800 can function as a radio transceiver providing and receiving radio signals. In a preferred embodiment, the radio signals provided by the mobile communication device 800 are smartcard compatible signals. FIG. 8 depicts a partial cut-away view of a mobile communication device 800 in accordance with another exemplary embodiment of the invention. In this embodiment, the mobile communication device 800 includes a radio conversion circuit 810 and antennae 850, 860.

The conversion circuit 810 is electronically coupled to a communication bus or processor of the mobile communication device 800 through communication paths 812. Radio conversion circuit 810 converts electronic signals received on communication paths 812 to radio frequencies that it provides on one or both of antennae 850, 860. Radio conversion circuit 810 converts radio frequencies received on one or both of antennae 850, 860 to electronic signals provided on communication paths 812. The two communications paths 812 shown are intended to be representative of any number of communications paths appropriate to exchange electronic signals between the conversion circuit 810 and other part of the mobile communication device 800 (e.g., a data path or processor). Although shown with the conversion circuit 810 coupled to antennae 850, 860, the conversion circuit is coupled to and utilizes the antennae 817 of the mobile communication device 800 and one or both of the antennae may be eliminated. The antennae 850, 860 are tuned to provide signals compatible with the smartcard.

Unlike the smartlink modules 100, 600 described in reference to FIGS. 1 and 6, the mobile communication device 800 does not follow conventional smartcard communication standards requiring that the a device operating in one of either contact or contactless mode at a time (e.g., ISO standards 7816 and 14443). The mobile communication device 800 operates as a smartcard transceiver eliminating the process of switching between contact and contactless operation modes. In the current embodiment of the invention, the mobile communication device 800 does not need to switch between contact and contactless operation.

Figure 9:
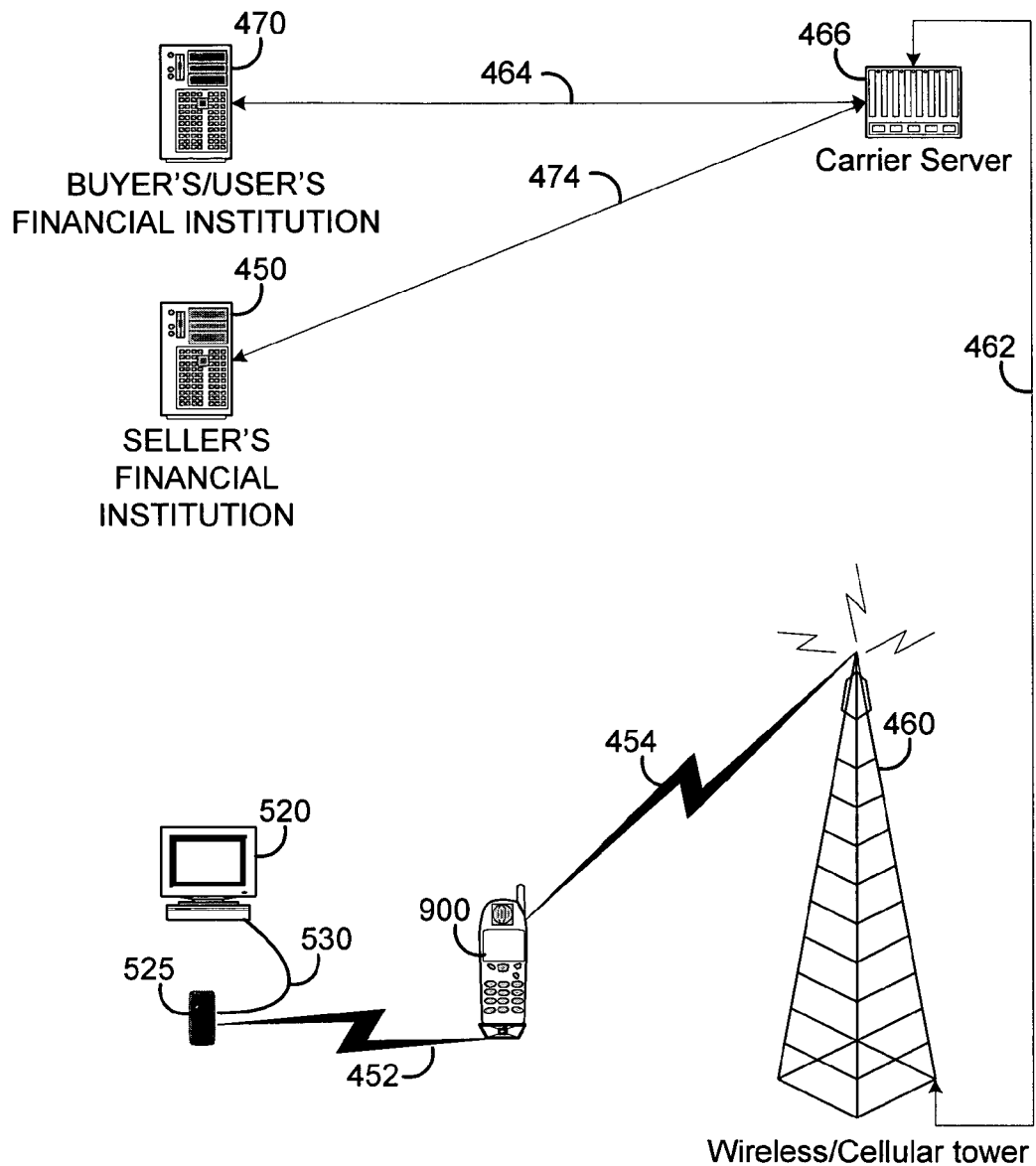
FIG. 9 shows a smartlink capable device acting as a digital cash register in accordance with yet another exemplary embodiment of the invention.

In another embodiment of the invention, as seen in FIG. 9, a smartlink capable device 900 (i.e., this can be any device described above with reference to FIGS. 1–8, including the mobile communication device 110 and smartlink module 100, the mobile communication device 110 and the smartlink module 600 or the mobile communication device 800) is depicted as a digital cash register which provides communication to the financial institutions of both the user and the other party. This embodiment of the invention differs from the previous embodiments in that with reference to FIG. 1–8 the POS device 420 communicates with the seller's financial institution server 450 to process the transaction and determine whether the transaction was approved. In this embodiment, the smartlink capable device 900 communicates with the user's and the seller's financial institution server 470, 450 to process the transaction and determine whether the transaction was approved. Further, the POS device 520 communicates to the seller's financial institution server 450 through the user's smartlink capable device 900 combination device. The POS device 520 is similar to a conventional point of sale device, however it uses the smartlink capable device to provide communication to the seller's financial institution server 450 to attain approval which is subsequently provided to the seller's POS device. The seller's POS system may later communicate with the seller's financial institution.

In another aspect of the invention the seller's POS may have limited communication and after the user's smartlink capable device provides the transaction information and the transaction is approved, the seller's POS receives a digital signal from the seller's financial institution indicating that the transaction is approved. The digital signal may be in the form of an SMS.

In a preferred embodiment, the signal to contact the seller's financial institution is transmitted by the user's smartlink capable device at substantially the same time the smartlink capable device 900 transmits a signal to contact the user's financial institution server 470. For example, both the seller's and the user's financial institutions 450, 470 are contacted, where the signal 454 to contact the seller's financial institution server 470 is "piggy-backed" to the signal to contact the user's financial institution server 450.

The POS device 520 contains a contactless relay circuit 525, e.g., a contactless Smartcard reader/writer, that receives and transmits wireless signals in substantially the same frequency as conventional Smartcard systems. The relay circuit 525 transmits a sales request signal requesting payment. In a preferred embodiment, the sales request signal from the relay circuit 525 includes transactional information, e.g., the cost of the transaction, the identification of the payee of the sales transaction, e.g., the seller, and additional identifying information of the sales device 520. The relay circuit 525 may receive a sales status signal indicating the payment has been made. The relay circuit 525 may also receive a sales status signal indicating the payment has been denied. The relay circuit 525 continuously transmits the sales request signal. Alternatively, the relay circuit 525 can be activated by the user pressing an activation button or requesting a specific item on the vending machine. In response, the vending machine will request a form of payment, transmit a sales request signal, and begin to look for a signal from a smartlink or the user's smartlink capable device 900. Further, the relay circuit 525 continuously checks if a sales status signal has been transmitted by a smartlink capable device 900. As indicated above, since a contactless smartlink communication system typically has a short communication range, in order to effectively communicate between smartlink capable device 900 and a relay circuit 525, the smartlink capable device 900 and the relay circuit 525 are placed in close proximity.

The smartlink capable device 900 receives the sales request information signal from the relay circuit 525. The smartlink capable device 900 queries the user whether they are interested in conducting the transaction. If the user is interested, then the user enters his/her PIN number indicating agreement.

Using the identification of the payee received from the relay circuit 525 as part of the sales request signal, the smartlink capable device 900 contacts the user's financial institution, and sends a signal requesting funds be transferred to the payee in the amount of the cost of the transaction. For example, if cash is the tender, then cash is transferred from the user's bank to the payee's financial institution, where the payee's financial institution is identifiable as part of the identification of the payee of the sales transaction. The user has previously established at least one financial institution, and relevant account information, to be used for the transfer of funds. If more than one financial institution has been established, then the user determines either before or during a transaction, which financial institution will serve as the user's source of payment. When the transfer of funds has been successfully completed from the user's bank to the payee's financial institution, the user's bank provides a signal to the user's smartlink capable device 900 indicating that transfer payment has been made.

The smartlink capable device 900 also communicates with the financial institution of the payee. Similar to communicating with the user's financial institution, the smartlink capable device 900 uses payee information (e.g., payee identification, identification of payee's financial institution) received from the sales device and initiates communication with the payee's financial institution. In this embodiment, the smartlink capable device 900 combination device provides communication to both the user's and the payee's financial institution and therefore provides the identifying address of two financial institutions to the smartlink capable device 900's wireless communication server. Although described with reference to communicating with two financial institutions, the number of financial institutions that the smartlink capable device 900 can communicate with depends on the implementation and can vary. This information may also be provided to a third party or a third party server (which may use the transaction information for other purposes, e.g., or marketing information, or to schedule supply or repair information).

When the payee's financial institution receives the appropriate amount of funds from the user's financial institution, the payee's financial institution provides a signal to the user's smartlink capable device 900 indicating that the appropriate funds have been received and provide a signal indicating the approval of the sales transaction. The smartlink capable device 900 provides a sales status signal to the relay circuit 525 of the sales device indicating that payment has been successfully made and been approved. Therefore, a smartlink capable device 900 requests the back end processing for the POS device and the POS device receives a signal from the smartlink capable device 900 indicating that the sales transaction has been approved by the POS's financial institution.

For example, a wireless relay circuit 525 is incorporated as part of a payment system of a soda machine, where the payment for the purchase of soda is done electronically (as opposed to conventional soda machines where payment is done with the use of coins and bills and the payment system is receives money, provides change and enables a purchase). The user activates a secure transfer program on his smartlink capable device 900 and places the smartlink capable device 900 in close proximity to the relay circuit 525 of the soda machine The relay circuit is part of the soda machine's payment mechanism (which in conventional applications processes coins and bills). The smartlink capable device 900 receives a sales request signal from the relay circuit 525 in the soda machine. The smartlink capable device 900 displays the cost of the transaction and queries the user for approval or simply displays the transaction and may not state the amount, just the transaction. Assuming the user continues to be interested in a soda, the user enters his PIN number into the smartlink capable device 900. The smartlink capable device 900 communicates with the user's financial institution to transfer money for soda to the payee's (e.g., the owner of the soda machine) financial institution. When the transfer of funds from the user's financial institution to the payee's financial institution is complete, the user's financial institution signals the user's smartlink capable device 900 that the transaction has been successful. Confirmation of the transfer may also be sent to the user via an SMS. After the user's smartlink capable device 900 receives a signal confirming the transfer of funds, the smartlink capable device 900 provides the sales status signal to the relay circuit 525 in the soda machine. In a preferred embodiment, the sales status signal is a digital token that allows a purchase for a specific amount of money. Generally, the amount of money will be predefined. After the relay circuit 525 receives the sales status signal confirming the transfer of funds, the relay circuit 525 of the soda machine enables the user to select a soda which will then be provided to him. In other aspects, the soda machine may have different prices for each soda.

Figure 10:
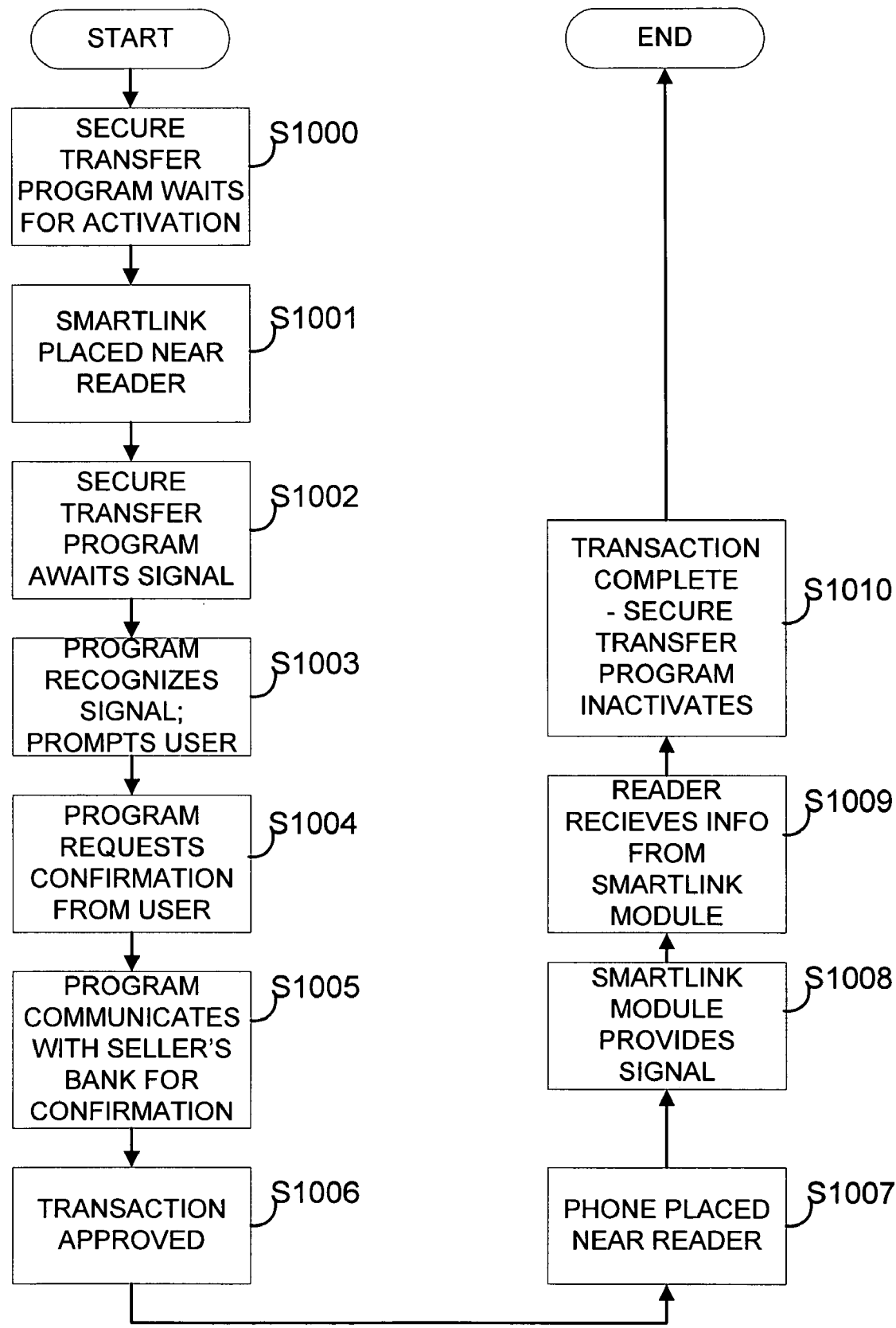
FIG. 10 shows a flow chart depicting a method of use of an exemplary embodiment of the invention in a vending machine context.

FIG. 10 depicts a flow chart indicating a method of use of the exemplary embodiment of the invention in a vending machine context. The process 1000 proceeds as follows:

In segment S1000, the secure transfer program runs as a background process in a mobile communication device waiting for activation. The precursor steps are that the customer interested in purchasing an item from a vending machine approaches the machine.

In segment S1001, the user's smartlink capable device 900 is placed near the device 525. The device 525 transmits a signal that can be received and recognized by the smartlink capable device 900. The transmitted signal may be, for example, the unique identifying information of the vending machine. This information may also include identification of a computer network/server associated with the vending machine.

In segment S1002, the secure transfer program awaits a signal from the device 410. When a signal is received from the device 410, then the process continues to segment S1003.

In segment S1003, the secure transfer program recognizes the signal from the device 410 and sends a handshake signal back to the device 410 as is conventionally known. The device 410 then sends a signal to the secure transfer program of the smartlink capable device 900 for additional information. For example, the signal may indicate the purchase price upon which the smartlink capable device 900 displays the purchase price of the goods. The secure transfer program then prompts the user to see if the user agrees with the purchase price.

In segment S1004, the secure transfer program of the smartlink capable device 900 requests additional information from the user. If the user agrees to the purchase price, the secure transfer program requests the user input her/his unique PIN number. If the user agrees and enters the appropriate PIN number, then the secure transfer program extracts the secure financial data information, e.g., the credit card number and associated transaction information that is stored in the smartlink capable device 900. The secure transfer program, using the user's personal information, establishes communication with the user's financial institution and requests the transfer of funds. Once the request is complete and accepted, process continues to segment S1005.

In segment S1005, the secure transfer program, using the information received from the vending machine, communicates with the seller's financial institution to receive confirmation or approval of the sale. In segment S1006, if the transaction has been approved by the seller's financial institution, the seller's financial institution then sends a signal to the secure transfer program. In segment S1007, the user is prompted to place the smartlink capable device 900 near the vending machine and within communication range of the relay circuit 525.

In segment S1008, the secure transfer program of the smartlink capable device 900 enables a signal to the vending machine to the relay circuit 525 of the vending machine 520. This signal may include the approved purchase price and may also include a security encoding or confirmation to reduce the vending machine receiving illegitimate confirmation signals. In segment S1009, the vending machine receives the signal from the smartlink capable device 900 approving the transaction and permits the purchase. In segment S1010, the transaction is complete and the secure transfer program awaits another signal from a device 410 to indicate commencing another transaction. Thus, at the completion of the process 1000, the user has purchased an item from a vending machine.

Figure 11:
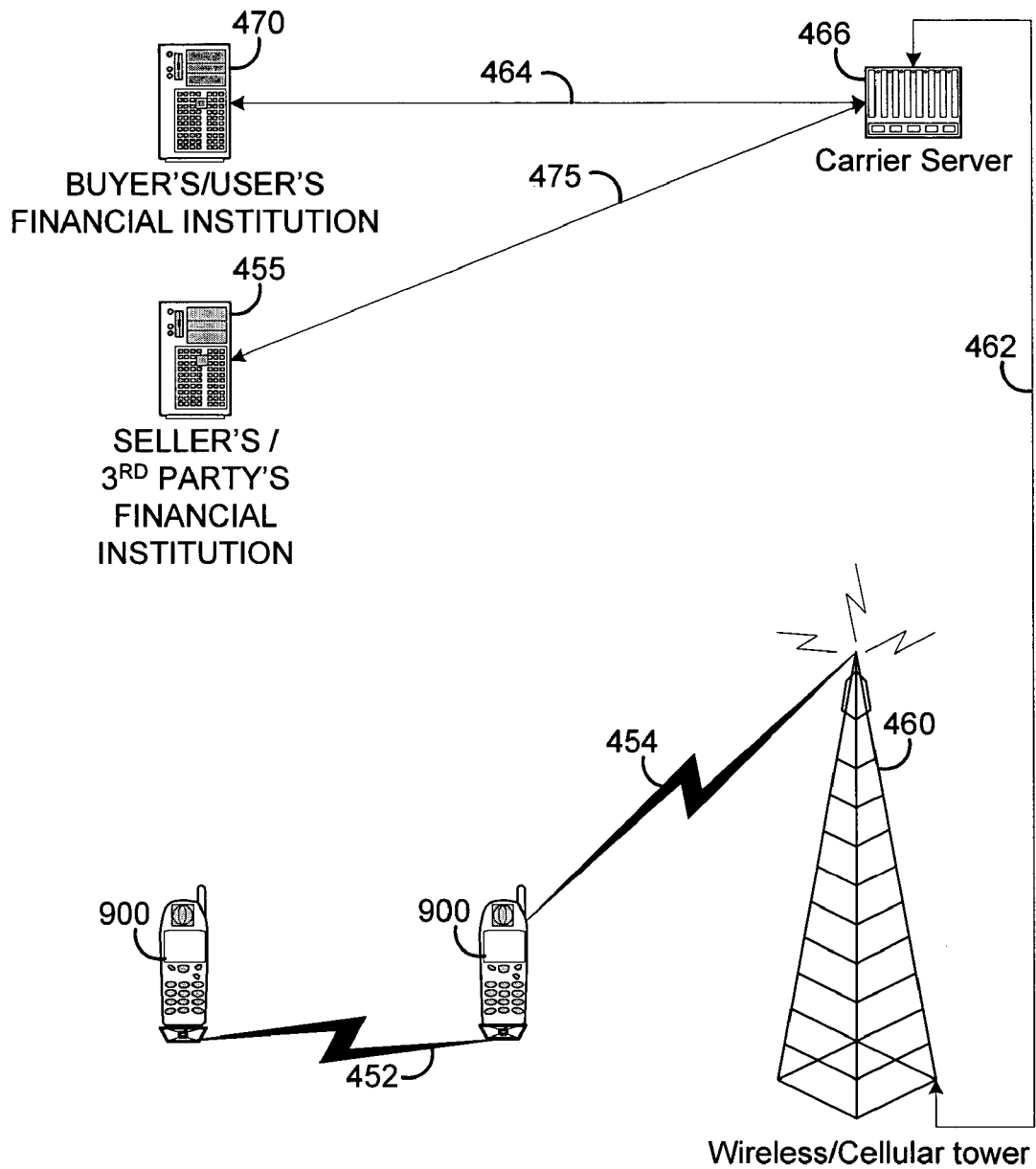
FIG. 11 shows a smartlink capable device used in a transaction in accordance with another embodiment of the present invention.
Figure 12:
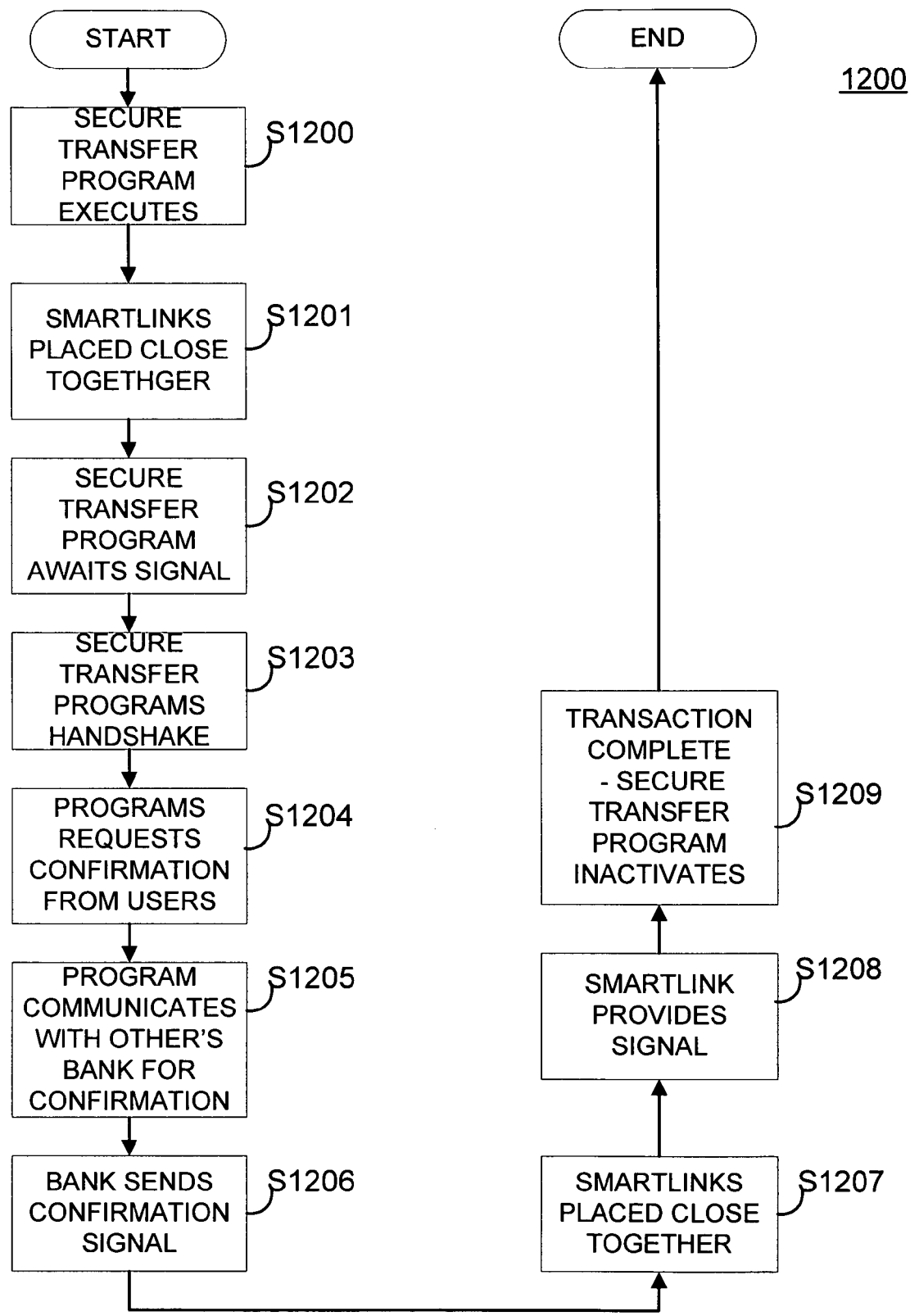
FIG. 12 shows a flow chart depicting a method of use of an exemplary embodiment of the invention in with a device as depicted in FIG. 11.

FIG. 11 shows a smartlink capable device 900 used in a transaction according to another embodiment of the present invention. The operation of the smartlink capable device 900 combination described with reference to FIG. 11 differs from the operation of the smartlink capable device 900 of FIG. 10 in that the smartlink capable device 900 communicates with and conducts a financial transaction with a second, e.g., a third party's, smartlink capable device 900. Similar to the FIG. 10 operation, the first smartlink capable device 900 is responsible for initiating communications to the user's and third party's financial institution. The process 1200 would proceed in the following steps (as show in FIG. 12):

In segment S1200, the secure transfer program runs as a background process in a smartlink capable device 900 waiting for activation. In segment S1201, the user's smartlink capable device 900 is placed near the other person's smartlink capable device 900. The other person's smartlink capable device 900 transmits a signal that can be received and recognized by the user's smartlink capable device 900. In one aspect of the invention a secure transfer program of each party of each party must be initiated by the respective party and automatically controls the transaction. In another aspect of the invention, each party initiates the secure transfer program and designates information necessary to the transaction (e.g., who is the sender, receiver, amount, etc.). The transmitted signal may be, for example, the unique identifying information of the other person's financial institution. This information may also include identification of a computer network/server associated with the other person's financial institution.

In segment S1202, the secure transfer program of the user's smartlink capable device 900 awaits a signal from the other person's smartlink capable device 900. When a signal is received from the other person's smartlink capable device 900, the process continues to segment S1203.

In segment S1203, the secure transfer program recognizes the signal from the other person's smartlink capable device 900 and sends a handshaking signal back to the device 410. The device 410 then sends a signal to the secure transfer program for additional information. For example, the signal may indicate the transfer amount (e.g., currency and value) and whether the funds are to be sent or received. The user's mobile communication device 110 displays the transfer amount. The secure transfer program then prompts the user to see if the user agrees with the transfer amount. The process continues to segment S1204.

In segment S1204, the secure transfer program requests additional information from the user. If the user agrees to the transfer amount as displayed on the mobile communication device 110, the secure transfer program requests the user input her/his unique PIN number. If the user agrees and enters the appropriate PIN number, then the secure transfer program extracts the secure financial data information, e.g., the credit card number or debit card number, etc and associated transaction information that is stored in the mobile communication device 110. The secure transfer program, using the user's personal information, establishes communication with the user's financial institution and requests the transfer of funds. Once the request is complete and accepted, process continues to segment S1205.

In segment S1205, the secure transfer program, using the information received from the other person's mobile communication device 110, communicates with the other person's financial institution to receive confirmation or approval of the transfer.

In segment S1206, if the transaction has been approved by the other person's financial institution FIG. 4, the other person's financial institution sends a signal to the secure transfer program.

In segment S1207, the user is prompted to place the smartlink capable device 900 near the other person's smartlink capable device 900 and within communication range of each respective smartlink capable device 900.

In segment S1208, the secure transfer program transmits a signal to the other person's smartlink capable device 900 through the smartlink 110. This signal may include the approved transfer amount and may also include a security encoding or confirmation. In segment S1209, the transaction is complete and the secure transfer program awaits another signal from a device 410 to indicate commencing another transaction.

Thus at the completion of the process, information (money) is transferred from one party to another party.

Figure 13:
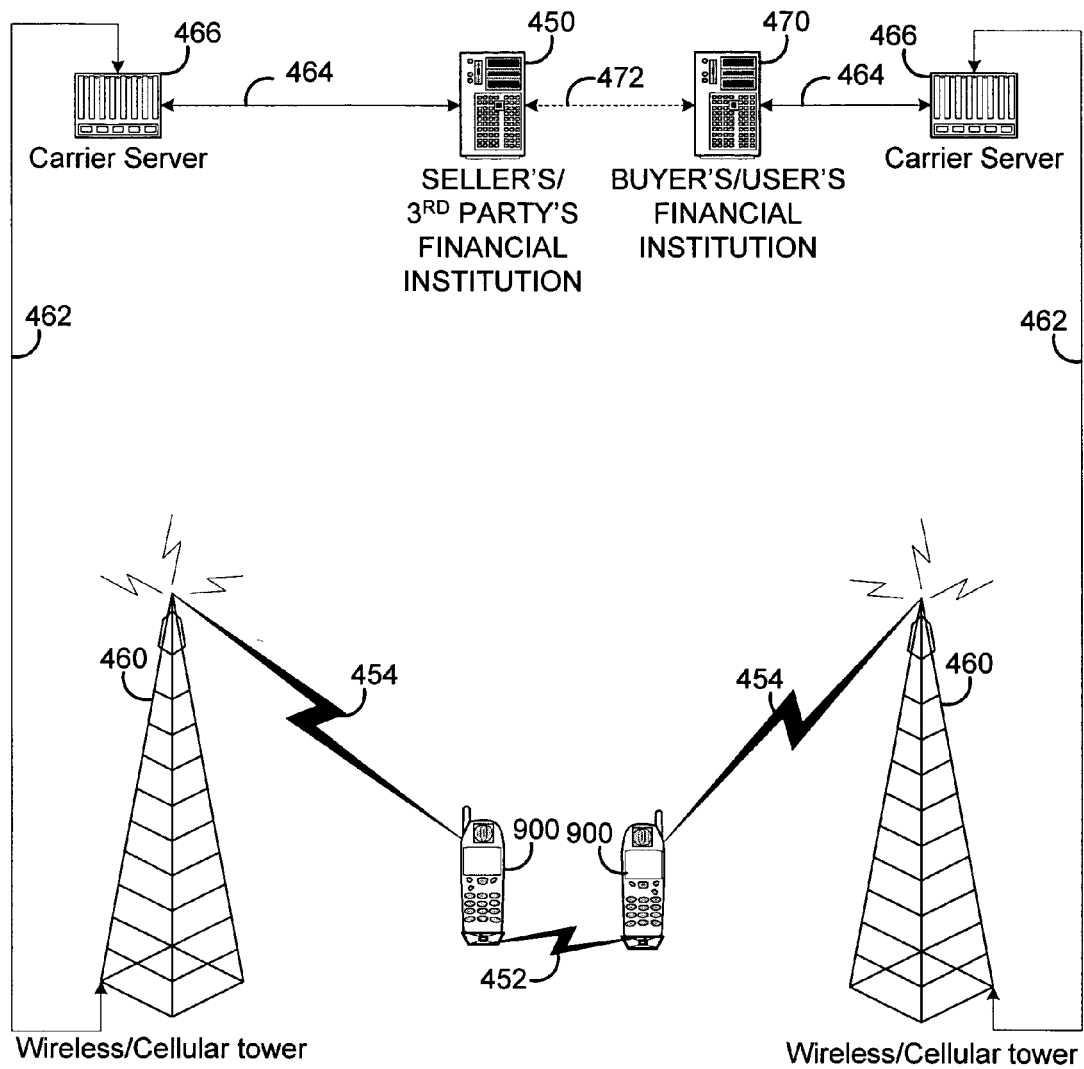
FIG. 13 shows a smartlink capable device used in a transaction in accordance with yet another embodiment of the present invention.

FIG. 13 depicts a further embodiment of the smartlink capable device 900 device. This embodiment differs from the embodiment described with reference to FIG. 11 in that in this aspect each smartlink 110 and mobile communication device 100 combination device uses its respective wireless carrier to communicate with its respective financial institution, 470, 450.

The methods and devices and device combinations provided can be applied to a variety of applications where increased security is sought for data transfer.

In an exemplary use, secure data transfer is used in a Point of Sale transaction. Upon initiating point of sale, the user will be prompted by a secure transfer program of their mobile communication device to enter their PIN number and press ok. When the user puts in the PIN number, the user is then instructed to tap the mobile communication device to the reader of the seller. The user will have a defined period of time before the mobile communication device defaults back into normal security mode and restricts any information of the user to be read. Once the user has tapped the mobile communication device and given the reader its information, the normal credit card processing begins. At the end of the processing, the user will receive an SMS or Email receipt onto their mobile communication device to confirm the transaction which will have details such as time, date, amount, store, etc.

In another aspect, the secure transfer program is automatically activated when the user taps the mobile communication device to the reader. The secure transfer program will automatically recognize that this is a point of sale transaction and initiate the point of sale sub-application.

In an exemplary use, secure data transfer is used in a vending machine transaction. The user has the option of purchasing an item from the vending machine by either using cash money or smartlink. For example, the user will activate the secure transfer program on his mobile communications device and select the sub-application Vending Machine. Once the Vending Machine is selected, the user will be instructed to tap mobile communication device to the reader, which is on the vending machine. The mobile communication device will then receive the vending machine's ID, bank information and marketing and servicing data such as the current amount of items sold and the vending machine's temperature. After smartlink receives this data, the user will be instructed to enter the amount they wish to purchase, then pressing ok, then enter their PIN number and press OK. Smartlink will then send back a signal via the Internet. Since the user and vending machine's financial institution will be communicating with each other and with the phone, the user's mobile communication device will receive an SMS receipt to confirm completion of transaction, which will include the amount purchased, vending machine's ID, date and time of the transaction. The method of using includes a user: selecting Vending Machine application from the Secure Transfer Program of the user's mobile communication device; tapping the mobile communication device on reader; entering the amount to purchase and pressing Ok; entering the amount and PIN number and pressing OK; receive authorization; and then tapping the mobile communication device to reader. Then the vending machine will activate and the user selects an item. The Secure Transfer program waits for a SMS receipt.

In another exemplary use, secure data transfer is used in an arcade transaction. The Arcade Application is similar to the vending machine example and not only gives the user the option paying the arcade through smartlink, but also permits uploading the user's score and position in arcade games that are played. The mobile communication device will automatically select the Arcade Application from the secure transfer program. Once the Arcade Application is automatically selected, the user will enter the amount to be purchased and will press OK. The user will then enter his/her PIN number and press OK. When the transaction is approved, the user will tap the mobile communication device on reader again to start playing. The user will receive an SMS receipt confirming transaction completion, which will include the amount purchased, arcade, date and time. Then the mobile communication device will give the option to upload existing position. The user will press OK and tap the mobile communication device on reader located on the arcade, if he wishes to do so. The user will also press OK and tap the mobile communication device on reader to download the ending score. The phone will inform the user that the score has been uploaded. A method of use includes the user: tapping his mobile communication device on reader located on the arcade machine and mobile communication device will automatically select application; entering the amount to be purchased and pressing OK; entering PIN number and pressing OK; tapping the mobile communication device on reader; waiting for an SMS receipt (where the receipt will show transaction completion including amount, arcade, date and time of transaction); pressing OK and tapping the mobile communication device to the reader on arcade machine to upload information (e.g., existing position); pressing OK and tapping mobile communication device to the reader on arcade to upload existing score. The mobile communication device will inform user that the score has been uploaded on the mobile communication device.

In an exemplary use, secure data transfer is used in a parking meter transaction. The Parking Meter Application allows the user to pay the parking meter by using smartlink instead of cash. For example, once the user park his car, he will activate the secure transfer program. The mobile communication device will instruct the users to tap the mobile communication device on the reader associated with a parking meter and then will automatically select Parking Meter as the sub-application. The user will then enter his PIN number and press OK. The secure transfer program will instruct the user to tap the mobile communication device again to begin the transaction. The mobile communication device time will start to run. Once the user returns to the car, he will select to end transaction of the secure transfer program of the mobile communication device. The mobile communication device timer will stop and the user will be instructed to tap the mobile communication device on the reader of the parking meter to complete the transaction. The timer will only stop for a few seconds but will start up again if the user does not tap the mobile communication device to complete transaction. When the transaction is complete, the mobile communication device will communicate with the smartlink server to carry out the financial transaction with the server of the parking meter. The user will receive an SMS receipt confirming completion of transaction, which will include amount, parking period, parking meter, date and time. A method of use includes the user: selecting the secure transfer program; tapping the mobile communication device to the reader of a parking meter and the mobile communication device will automatically select parking meter application; entering his PIN number and pressing OK; tapping the mobile communication device to parking meter to start the clock running; selecting end transaction; tapping the mobile communication device to the reader of the parking meter to complete transaction; waiting for an SMS receipt; and receiving an SMS receipt which confirms the transaction completion, which will include amount, parking period, parking meter, date and time.

Another example of an application of the invention is a person to person financial exchange. Person-to-person is a method of exchanging currency in a digital mode with two smartlink enabled devices. The process is designed to mimic a paper currency transaction but in a digital and thus secure form. During the money exchange process, the users will have the option of activating smartlink for giving or receiving money. Upon selecting the person to person process under the secure transfer program and selecting whether they wish to send or receive money, users will be instructed to enter the amount they wish to transfer or credit along with their individual pin numbers. Once users respectively enter their pin numbers and press ok, they will be instructed to tap mobile communication devices. The mobile communication devices will communicate with their respective smartlink servers to coordinate the financial transaction between financial institutions. The users will then receive an SMS receipt confirming completion of transaction which will include the name of the person to whom they sent or received money, the date and time of the transaction. The method of using includes the user: selecting the person-to-person application; selecting "send" or "receive"; if the user is the sender of the funds, entering the amount to be transferred and his PIN number; if the user is the receiver of the funds, entering pin number; pressing OK; tapping each mobile communication device to each other's smartlink. The financial institutions are contacted via the cellular link, and transaction processing is done between the server's of the financial institutions and an SMS receipt is respectively received by each party confirming the transaction.

Another exemplary use of the present invention in is a grocery information transaction occurs. The Grocery Information application provides a user with the option of finding product information, price comparison, and coupons by activating smartlink. For example, the user will activate the secure transfer program on his mobile communication device and then select the sub-application Grocery Information. The secure transfer program will instruct the user to tap mobile communication device on an RFID tag of a product. Once the mobile communication device is tapped, it will give the user three options: Details, Comparisons, and Coupons. By selecting "Details" the user will be given product details such as manufacturing location and nutritional information. By selecting "Comparisons" the user will be given price comparisons between alternative brands. Information about the product can be provided by an RFID tag directly or by using the product identifying information determined by the RFID tag and getting the information from an appropriate server. By selecting "Coupons" the user will be informed of any available coupon for that particular product. The coupon value can then be automatically deducted from the user's bill during a Point of Sale transaction. A method of use would include the user: selecting grocery information; tapping the mobile communication device on the RFID tag; selecting among several options: Details (Options 1), Comparisons (Option2), and Coupons (Option 3). Depending on the option, the secure transfer program will inform user of: product details such as manufacturing and nutritional information; price comparisons between products (e.g., chosen and other alternative brands), or will inform of any available coupon for that product, which will be automatically discounted during the Point of Sale process, respectively.

Digital Coupon are another example of a use of the present invention. The Digital Coupon transaction allows a person to find any available coupons for a particular store and to use it towards their purchase or define specific coupons at that store for that specific individual. Upon entering the store, a user will be able to use smartlink to verify the existence of coupons for that particular store. For example, the user will the activate secure transfer program and select the sub-application "Digital Coupon." The user will be instructed to tap the mobile communication device to a reader of the store and the mobile communication device will inform the user of any particular coupon for that store. Once the purchase is made and the Point of Sale process initiated, discount can will be taken automatically for a transaction.

In yet another exemplary use, the present invention is used for purchasing products at home (e.g., grocery purchases). The Home Grocery Buying Application allows a user to purchase an item from home through the smartlink system. For example, the user will activate secure transfer program and select the sub-application Home Grocery Buying. The mobile communication device will instruct the user to Tap Phone on RFID Tag of the selected product that is sought to be purchased. The mobile communication device will further instruct the user to press OK to complete transaction or to press Next to purchase another product as well. Once all products are ready to be purchased, mobile communication device will give the user an option to have purchase delivered to the user's address or pickup items at store. The user will then enter a PIN number and press OK. The mobile communication program will inform the user of a location or store that can service the user and may be provided a choice of stores. The user will select the store they want to purchase the items from. The smartlink server will communicate with the server of the selected store and the user will receive a SMS receipt upon transaction completion, which will include amount purchased, store, date and time. A method of use includes a user: selecting Grocery Information Application; selecting the Home Purchase option; tapping a mobile communication device to a product; pressing OK to complete transaction or next (to purchase another product); selecting an option to complete transaction; pressing OK to have purchase delivered to the user's address or to pickup; entering his PIN number and pressing OK; selecting a store to service the order (e.g., among three nearest locations); waiting for an SMS receipt. The user receives an SMS receipt confirming transaction completion information including amount, store, date and time.

Figure 14:
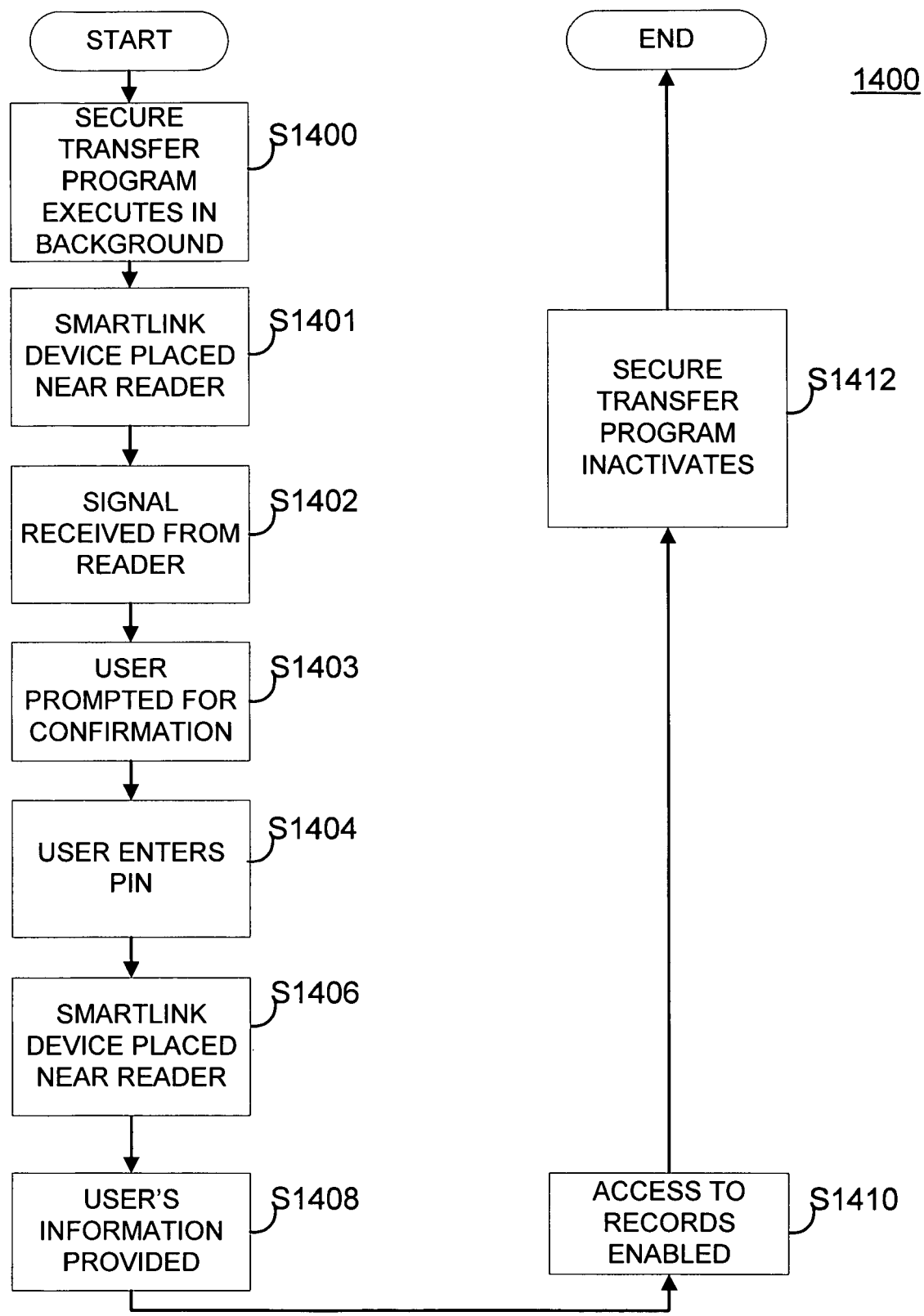
FIG. 14 shows a flow chart depicting a method of use of an exemplary embodiment of the invention.

In an exemplary use, Medical chart/information use confirmation process occurs. The Medical Charts Application will allow user to digitally transfer insurance and/or medical information during a visit to the doctor. For example, a user will activate his secure transfer program on his smartcard capable device (e.g., smartcard capable device 900) upon reaching the front desk of the doctor's office. The doctor's office computer executes a program that connects the doctor's office computer to a third party server, e.g., a medical records server or insurance company server. (e.g., the program may be a web application that the Doctor's office has accessed through the Internet.) The user will tap the smartcard capable device on a smartcard reader connected to the doctor's medical office. The secure transfer program will receive a signal from the smartcard reader and determine the context (e.g., medical office) and automatically select the Medical Records option. In response to being prompted, the user will enter his PIN number into his smartcard capable device which will provide access to the user's personal information stored in the smartcard capable device. The user will tap the smart capable device again thereby transferring his personal information (e.g., name, social security number and information access certificate) to the reader. The smartcard reader provides the user's personal information to the doctor's office computer. The doctor's office computer, through its connection to the third party server, provides the user's personal information and identifying information of the doctor's office (e.g., name and IP address) to the third party server. The third party server compares the user's information with information stored within the third party server, and if the user's records are a part of the third party server's records, then the third party server sends a confirmation signal back to the doctor's office through the internet and sends by cellular communication a confirmation signal to the user. The doctor's office now has electronic access to the user's medical records stored electronically at the third party server. The third party server will send, preferably by cellular communication, a signal to the user each time the doctor's office accesses the user's records. The user can also utilize his smartcard capable device to prevent the doctor's office from having any further access to the user's records. In this manner, the user can monitor and control the doctor's office access to the records. An example of a method of using this aspect of this aspect of the invention is seen in FIG. 14. The process 1400 would proceed in the following steps:

In segment S1400, the secure transfer program runs as a process in a mobile communication device as a background process.

In segment S1401, the user taps his smartcard capable device on to the device 710.

In segment S1402, the secure transfer program awaits a signal from the device 710. The transmitted signal may be, for example, the unique identifying information of the medical office. This information may also include identification of a computer network/server associated with the medical office. When a signal is received from the device 710, then the process continues to segment S1403.

In segment S1403, the secure transfer program determines the type of signal from the device 710 and selects the Medical Records Option. The secure transfer program prompts the user to confirm whether the user agrees with the medical office having access to that information (for access to the user's medical records).

In segment S1404, the secure transfer program requests additional information from the user. If the user agrees to the medical office's access to the user's information, the user enters his PIN number.

In segment S1406, the user taps the smartcard capable device to the Doctor's office reader, thereby providing his personal information to the reader.

In segment S1408, the reader provides the personal information to the Doctor's office computer server, which in turns provides this information to the third party server (e.g., the medical server).

In segment S1410, the third party server compares the user's information that is provided with the stored information of the user. If information agrees then the third party server sends a confirmation signal to the Doctor's office server confirming access to the user's medical records. The third party server also sends a confirmation signal to the user.

In segment S1412, the secure transfer program returns to executing as a background process.

Thus, the doctor's office is enabled to access the user's medical records at the third party server.

In another exemplary use of the present invention, a prescription process is provided. The Prescription Application offers the user a couple of options after the prescription is purchased, such as reminding the user to take a pill and providing the user with a refill option. The user activates the secure transfer program and the mobile communication device will instruct the user to tap mobile communication device on prescription label containing the RFID Tag. The mobile communication device will then automatically select the Prescription Application. Once the Prescription Application is automatically selected, the mobile communication device will give the user the option of selecting a schedule for a reminder to remind him/her to take his/her medication (e.g., an alarm clock, the user is reminded in the morning to take a pill.) The application can include a reminder for refilling the prescription. By using the refill reminder feature, the user can request that he be reminded a certain time period, a desired number of times, and certain times of the day before the prescription should expire. For example, one day before the user's pill supply is about to be depleted completely, the mobile communication device will ask the user if he/she would like to refill prescription. If the answer is yes, then the mobile communication device will order a prescription refill.

At that point, the secure transfer program communicates through it cellular capability with the user's pharmacy (e.g., the computer system of the user) to place an order for a refill of the prescription. The user will then receive a confirmation that the refill is being processed. An SMS will then give the order and pick up information indicating when the prescription is read for pickup. A method of use may include the user selecting the secure transfer program to select the refill prescription option; entering yes, pressing OK and the mobile communication device will inform the user that a refill is being processed. The user will receive an SMS receipt showing the order and pick up confirmation information. A method of use may includes a user: selecting the secure transfer program, tapping on the prescription label containing the RFID and the sub-application prescription is automatically selected, pressing OK to have secure transfer program remind the user of when to take a pill (based on quantity of prescription, recommended usage, and the precise times based on the first use of the pill and corresponding to the first use of the prescription application). To use this reminder service, the reminder is either an SMS from a cellular server or a reminder from an pill "alarm clock" on mobile communication device.

An access control system is provided as another exemplary use of the present invention. A user will have the option of using his key or smartlink to enable the user access to 'locked' system, which may be a door or any other similar scenario, including, for example, a computer. For example, the user will activate the secure transfer program and select a sub-application Access Control. The user will then be instructed to enter his/her PIN number and press Ok. Once the user enters the PIN number, the user will be instructed to tap mobile communication device on the reader on the door, the user's access information will be provided and the door will open. A method of use includes the user: selecting access control option, entering his/her PIN number and pressing OK; tapping the mobile communication device on reader (which is located on the door), and the door is enabled to open (e.g., the user is permitted access).

In the context of computer access which is secured by a smartlink system, when the user's logs on to a computer, the computer checks that the user is permitted access to the computer and determines if the user is part of a smartlink system. If the user is part of the smartlink system, then the computer sends a message to a smartlink server requesting confirmation and authentication of the user. This message includes the identification provided by the user. The smartlink server sends a message to the user (via SMS or digital means) requesting confirmation of access to the computer. If user confirms and sends a message to the smartlink server, then the smartlink server sends a confirmation message to the computer system. When the computer system receives confirmation signal from the smartlink server, then the user is granted access to the computer. Therefore, the computer does not directly contact the user to confirm access. The user is contacted indirectly, where the smartlink server serves as the connection between the computer and the user's smartlink capable device 900.

In the context of physical access to a secured area, the smartlink system is used to confirm identity. When a user attempts to enter an area secured by a smartlink system, the user places his smartlink capable device 900 close to the smartcard receiver transmitter that is coupled to a computer system controlling access to the secured area. After the computer system and the user's smartlink establishes communications, the user is prompted by the secure transfer program to enter his PIN. The secure transfer program unlocks secure access information stored within the smartlink capable device 900 and provides that information to the computer system. Upon receiving and confirming the user's access information the computer system enables the user's access to the secure area.

In another embodiment of the invention, a smartlink transaction is initiated by a third party. In this aspect, there are four elements of the system utilized to complete a transaction. A smartlink device, a smartlink server, a financial system, and the seller's system. The smartlink device, which in a preferred embodiment is a cellular mobile communication device, or a similar mobile communication device, is used by the customer to securely purchase items from a seller at a distance. As it is known, a customer seeks to purchase items from a non-brick and mortar environment where the customer does not visit the seller's actual location, but instead accesses the seller through a form of communication system, e.g., mobile communication device or Internet. After shopping and selecting certain items, the customer confirms and processes the purchases of the selected items from the seller from a distance by use of a communication device, coupled with smartchip similar to that described above. The seller's system is the computer system maintained or operated by, or for, a seller. A financial system is a method of financial payment that is correlated to the user of the smartlink device. The financial system may be, for example, a credit card, bank, or other financial institution. The seller may be, for example, a retail shop, an online store, or other brokerage and/or transaction broker.

Figure 15:
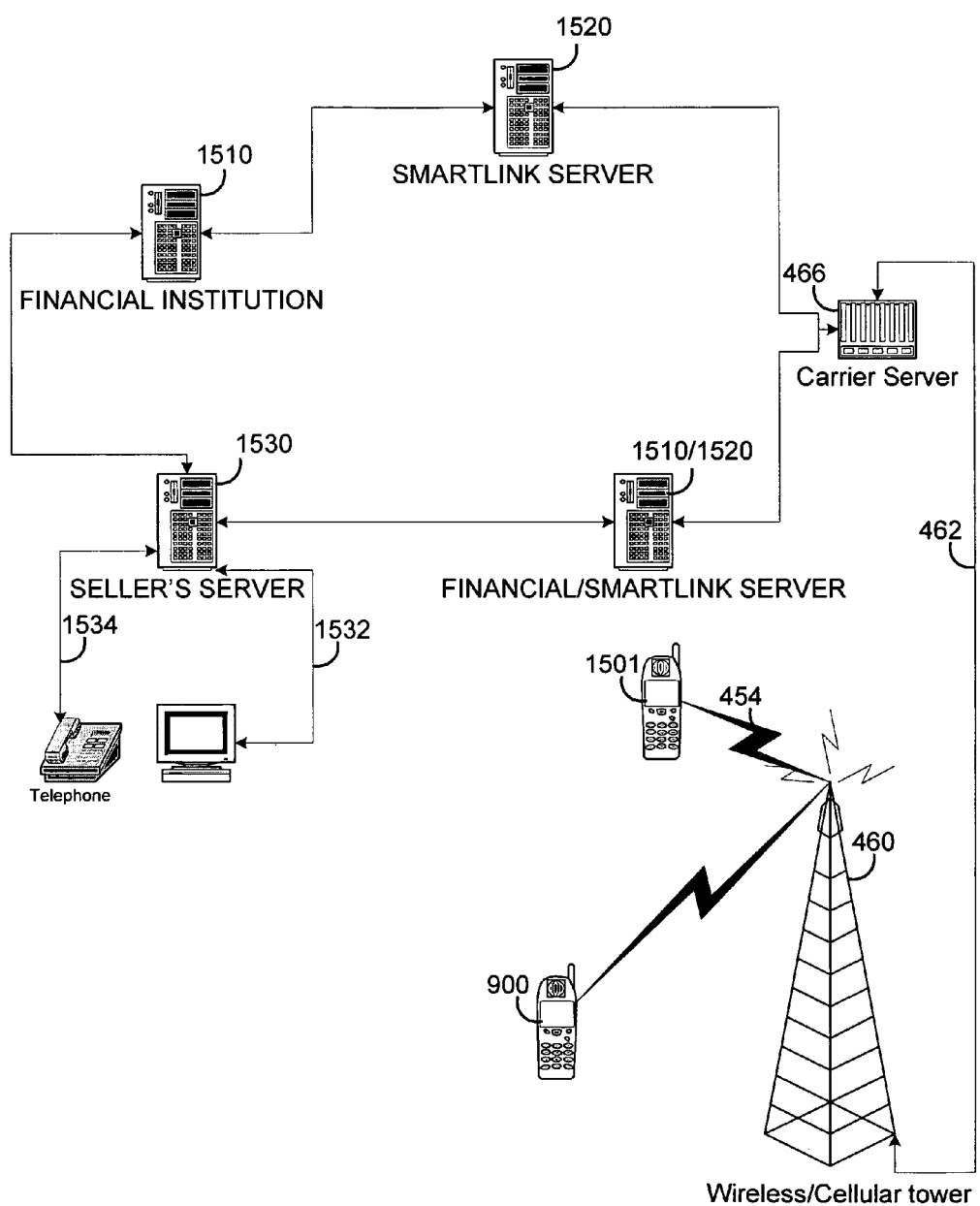
FIG. 15 shows a mobile communication device used in a remote transaction confirmation process in accordance with another exemplary embodiment of the invention.

A method of using the smartlink transaction is described with respect to FIG. 15. It is known for a customer to log onto the Internet and purchase items from stores on the Internet. Typically, the customer pays for the selected items by the use of a credit card by entering information into a web page or pages of the seller. Adding a smartlink transaction is initiated by a third party system. The security and reliability of the transaction is increased by strengthening the likelihood that a customer who is paying for a purchase with a financial instrument, e.g., a credit card, is also the owner of the credit card or acting under the authority of the owner of the credit card.

As seen in FIG. 15, there are four elements of the remote payment confirmation system. A smartlink device 900, a smartlink server 1520, a financial system server 1510, and the seller's system server 1530. The smartlink device 900, which in a preferred embodiment, is a smartlink capable device 900 similar to that described above. The seller's system server 1530 is the computer system maintained or operated by, or for, a seller. A financial system server 1510 is associated with the user's financial institution. The financial system may be, for example, a credit card, a bank, or an other financial institution. The seller may be, for example, a retail shop, an online store, or other brokerage and/or transaction broker. In this embodiment of the invention, a remote smartlink transaction is initiated by a third system, e.g., the seller's system 1530.

Figure 16:
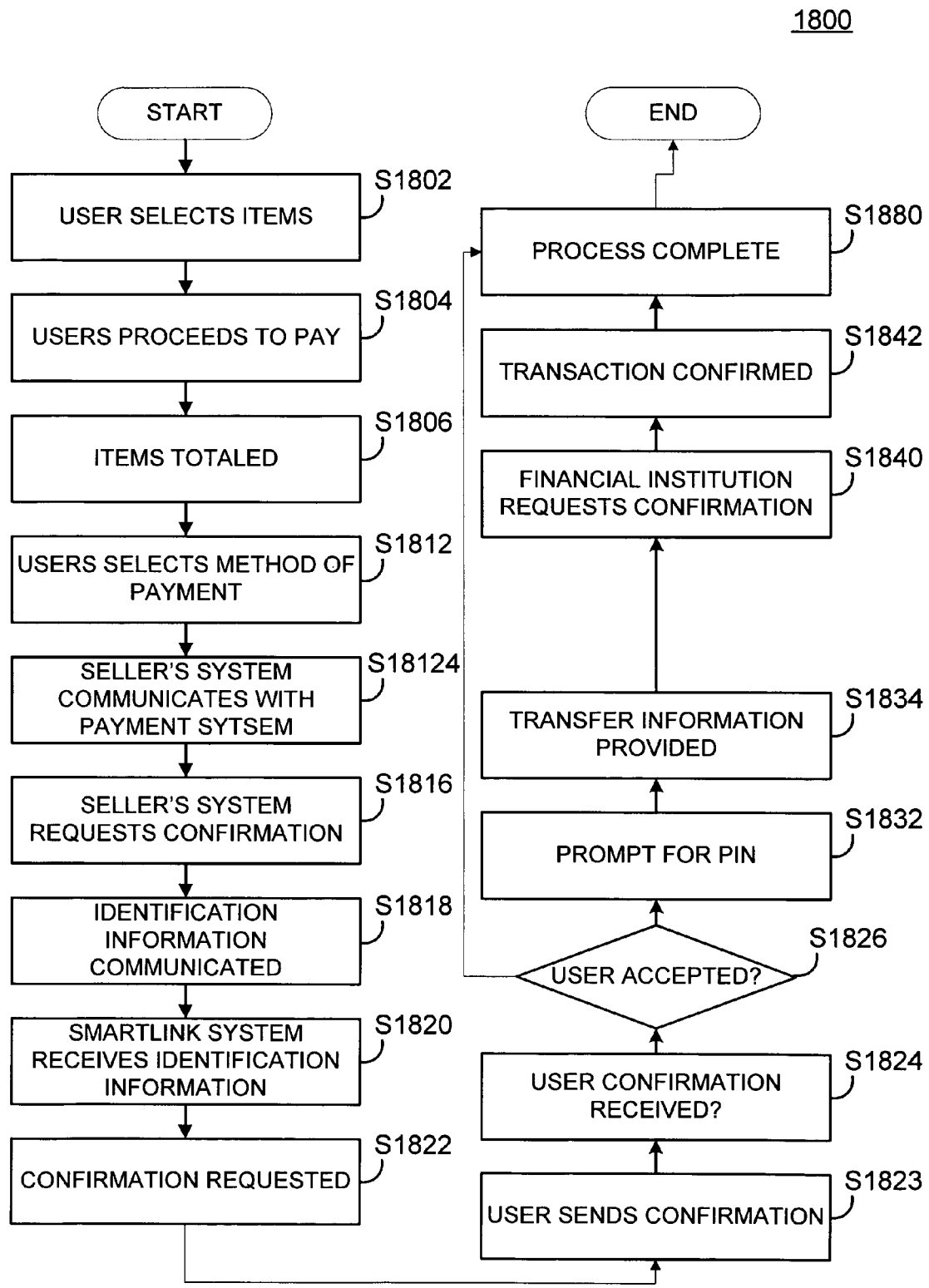
FIG. 16 shows a flow chart depicting a method of use of an exemplary embodiment of the invention in a remote transaction confirmation context.

A method of using the remote smartlink transaction is described with respect to FIG. 16. As seen in FIG. 16, in segment S1802, a user selects the item(s) that he wishes to purchase. If, for example, the seller is an e-merchant that is accessible on-line, the user may select a series of items from the choices provided by the seller and places them in his shopping cart. In another aspect, a user may contact and select items from a seller by mobile communication device. In segment S1804, the user proceeds to pay for the items chosen. In segment S1806, the selected items for purchase are totaled.

In segment S1812, the user selects a method of payment. In an on-line purchase environment, for example, the user will select his preferred method of payment by clicking on the icon representing the payment method or otherwise indicating his decision. In a mobile communication device purchase environment, for example, the user will select the payment method by telling the seller (or the seller's agent) his preferred method of payment. In a preferred approach, the user selects smartlink Financial as the preferred method of payment. The user's selection is received by the seller's system.

In segment S1814, the seller's system determines what method was selected or chosen by the user and communicates with the respective server of the payment method. For example, if the user chose VISA, the seller's system will communicate with the VISA server. If the user selected smartlink Financial as the method of payment, then the process continues to segment S1816.

In segment S1816, the seller's system requests identifying information from the user. The identifying information is used to associate the user with the transaction. The identifying information can be, for example, a smartlink account number or the user's mobile communication device number that the user desires to use for the transaction. In segment S1818, the seller's system communicates identifying information to a smartlink server. In segment S1820, the smartlink system receives the identifying information and determines the associated user.

In segment S1822, the smartlink server will send the customer—to the user's mobile communication device equipped with the smartlink system—a signal asking if customer had requested to purchase some items from seller and requests confirmation. In a preferred embodiment, this is a digital communication, mostly likely in the form of an SMS. In segment S1823, after receiving the SMS signal, the user can send a signal back to the smartlink system confirming the transaction. In one aspect, each item, and possibly the price, is displayed on the user's mobile communication device so that the user can confirm the purchase of each item. In another aspect, the seller's information is displayed and the total purchase price is presented for the approval of the user. In segment S1824, the smartlink awaits the confirmation signal(s) from the user. If, and when, the confirmation signal is received from the user, the process continues to segment S1826. In segment S1826, if user has declined, then the purchase is canceled.

In segment S1826, if user has accepted, then process continues to segment S1832. In segment S1832, the smartlink application will then request that the user enter his PIN number. In segment S1834, if the PIN number is accepted, then the smartlink application on the mobile communication device will unencrypt the information that is not unencrypted, and the information (which may be encrypted or unencrypted) is then sent to the financial server with acceptance certificates and the server unencrypts. The user's financial information stored in the mobile communication device and transmits it to the smartlink server. The user's information sent to the financial server will be encrypted. In general, the information sent to the financial server is, for example, an encrypted certificate and acceptance command as well as the user's information such as address, name, credit card number, etc. This information will typically include the user's billing and preferred shipping address as well as contact information (day and evening mobile communication device numbers, possibly even an email address). In this aspect, the user is not required to enter this information as part of a purchase, but the information is added to the purchase as part of the smartlink exchange of information with the seller's server.

In segment S1840 the financial institution's server communicates to the seller to confirm approval or the third party server's communicates to the financial institutions server to confirm the purchase and then the financial institution's server communicates to the sellers server (this assumes that the financial institution has also approved the transaction, i.e., that the user has a sufficient amount of funds or line of credit available for the desired transaction.) The process continues to segment S1842.

In segment S1842, once the transaction confirmation and approval is provided to the seller's server, the user is provided a signal, preferably a digital communication in the form of an SMS, reflecting that a purchase has been processed from a specific store and can include total amount, items, etc. The process continues to segment S1880.

In segment S1880, the process ends.

Thus, a remotely conducted financial transaction is confirmed by contacting the user associated with the payment method and receiving confirmation from him. In another aspect, the financial institution and the smartlink server are part of a single system. This is depicted in FIG. 15 as Financial/smartlink server 1510/1520. In yet another aspect a convention mobile user interface 1501 which does not include a smartlink module (FIGS. 1–7) or embedded smartlink (FIG. 8) is used place of a smartlink capable device 900 in a remotely conducted financial transaction as described with respect to FIGS. 15 and 16.

In another aspect of the invention, the user's smartlink system initiates and facilitates the processing of a financial transaction. The process is initiated when the user with a smartlink device approaches and taps (places it very close to) the smartlink device to the smartlink reader. The secure transfer program recognizes the process necessary that corresponding to the reader and starts that process. The user inputs their PIN to release encrypted information. The mobile communication device sends this information to the user's bank and to the seller's bank. Once the two banks communicate and the transaction is approved, one of the banks sends a signal to the user's mobile communication device with a certificate (to show authenticity) and an electronic token (which represents a certain value). The mobile communication device is tapped on the smartcard reader and sends this information to the smartcard reader/relay circuit. The smartcard reader processes the transaction if the certificate and the value are appropriate.

Many of the advantages of the present invention are apparent when looking at some of the many different applications of the present invention. Not limited to sales, the methods and apparatus described above can be used for any financial or information transaction, access control of systems and facilities, access or remote access to information warehouses such as medical database, etc. For example, the methods and apparatus described above can be used to transfer money from the user's account to another party's account, where the information necessary to conduct the transaction is transferred to the user's mobile communication device, by placing the user's mobile communication device in close proximity to the other party's mobile communication device. Both the user's mobile communication device and the other party's mobile communication device have secure cellular network connections to the financial institution's servers. All transactions can be tracked, so if a user provides another party with a balance transfer, the transaction is tracked to show where the funds are transferred to. As in conventional funds transfers, the user's and other party's financial institution records transactions, and the records of these transactions are maintained by the respective financial institutions.

In another aspect of the invention, the secure transfer program has more than one type of transaction that it can process. For example, the secure transfer program can process POS sales and also process access control. In an aspect, when the secure transfer program becomes active, (e.g., after receiving a signal in a smartcard frequency from a smartcard receiver/transmitter), the secure transfer program will prompt the user to select which type of process the user would like to conduct. Once selected, the secure transfer program then executes the appropriate process.

In another aspect of the invention, the secure transfer program will recognize the appropriate type of transaction that the user is most likely interested in conducting. In this aspect a signal from a smartcard receiver/transmitter will include an identification of the context or type of transaction system that it is a part of. When the secure transfer program is not already executing a process and it receives a signal from a smartcard receiving/transmitter, the program will examine the signal to determine if it contains information identifying the context of the transaction. If the signal does include contextual information, then the secure transfer program begins a confirmation process for that context. For example, in a point of sale context, the POS smartcard receiver/transmitter will transmit signals that includes a signal indicating that the context is POS. If the secure transfer program identifies the context as a POS, then the secure transfer program will commence the confirmation process.

While the invention has been described and illustrated with reference to specific exemplary embodiments, it should be understood that many modifications and substitutions could be made without departing from the spirit and scope of the invention, even though a particular embodiment is not specifically described. For example, the different processing segments described above are not limited to those segments or that order of segments, segments may be omitted and still maintain the spirit and scope of the invention. Although generally the description above refers to a processing chip, it should not be so limited and can include many other implementations and instrumentalities. The chip could be, for example, a microprocessor, an integrated circuit, transceiver, or module. Although the inventions above are generally described with respect to financial transactions, the invention is not intended to be so limited and can be used to increase the security of any type of data that can be stored in a mobile communication device. Although described as a mobile communication device and the invention is not so limited and can include various mobile user interfaces including cellular phones, mobile communicators, personal digital assistants, portable processing devices, keyboard, keypads, and biometric devices.

Additionally, although several different embodiments and aspects of the invention are described above, the methods of use are applicable to every variation of the invention although each embodiment may require a modification of the methods of necessary to be adapted to each invention. Further adaptation of the methods of use may be required for the use of the invention in different contexts.

Additionally, although examples are described with respect to the transfer of funds, the invention is not so limited and the implementation of the invention may also include acceptance of credit. For example, the user's financial institution may provide the seller with a indication that maybe will be made at a future date and seller's will accept this indication and permit a transaction to continue as if the money had actually been transferred. This most likely would be occur where the user's financial institution is a credit card company; the credit card company may not "pay" (transfer funds) contemporaneous with the user's purchase, but instead may transfer funds at a later time. Although not expressly indicated, the secure transfer program in each embodiment and/or aspect of the invention may be different. The program may also vary depending on the type and model of mobile communication device used. Further, there are different methods of confirming the processing (e.g., "getting approval") with the use of the embodiments described above, and the invention is not intended to be so limited. Although the embodiments are generally described with respect to a seller's computer system communicating with a financial institution, the invention is not intended to be so limited and the seller's system can communicate with more than one financial institution.

Additionally, in many of the aspects described above, a non communication device can be used in place of a mobile communication device. For example, a personal digital assistant can be coupled with a smartlink module. Furthermore, although the above descriptions refer to confirmation/authentication of an owner and/or user, the invention is not meant to be limited to the actual owner/user. For example, a user tells a third party his PIN number so that the third party can use the user's mobile communication device to perform a transaction. (e.g., purchase a soft drink). Although some of the inventions are described as having devices or circuit being in compliance with established standards, e.g., ISO standards, the invention is not intended on being so limited. For example, a mobile communication device may communicate with a smartlink processing chip in a contact mode following ISO standard 7816. However, the operating system in a mobile communication device maybe designed to communicate with the processing chip in a contact mode using any conventional communication standard.

Furthermore, in the processes/methods of use descriptions above, separate processes/segments may be combined into a single process/segments therefore reducing the number distinct processes/segments and visa versa; process that are represented as a single segment, may be broken down into a plurality of segments. When a description above refers to a transfer of money, this is not meant to be limited to an actual transfer of money, but may include other transfers including where the transferee may anticipate that the transfer will occur and approve the transaction before the money is transferred.

In the descriptions above, a secure transfer program may be a single program or application, a program/application with sub-programs and/or sub-applications, or it may be many programs and/or applications. A secure transfer program may have different requirements to properly execute the appropriate transaction process. For example, a secure transfer program for a vending machine context is likely to be different from a secure transfer program for a point of sale scenario. Additionally, the selection of the appropriate secure transfer program for a transaction context may be done manually by a user or it might be done automatically by a secure transfer program recognizing the context in which it is being used. An automatic recognition feature may be based on a secure transfer program recognizing and identifying a signal from a smartcard transceiver. For example, a secure transfer program of a mobile communications device will recognize the context as a vending machine when the mobile communication device is held close enough to the vending machine and the mobile communications device receives a signal from the vending machine and identifies that signal as coming from a vending machine.

Additionally, although not necessarily expressly stated in the embodiments and aspects of the invention described above, a smartlink system is intended to generally include a mobile communications device with a smartlink module, or smartlink module functionality, and a smartlink server. In the preferred embodiments, the smartlink server is a computer system which stores information of a user and can communicate with the mobile communication device of the user by cellular connection or other appropriate means. The smartlink server can communicate with third party computer systems (e.g., of a seller or other third party) to exchange information and/or to provide and/or receive payment.

Accordingly, the invention is not to be considered as limited by the foregoing description but is only limited by the scope of the claims.

What is claimed as new and desired to be protected by Letters Patent of the United States is:

1. A smartlink module, comprising:
   a smartcard chip for converting radio waves into electrical signals, for converting electrical signals into radio waves, said electrical signals being either analog or digital signals, said radiowaves being in the form of smartcard radio frequencies;
   a first data channel being adapted to wirelessly communicate data using an antenna between said smartcard chip and a third party terminal capable of transceiving smartcard radio signal, said first data channel coupled to said smartcard chip; and
   a second data channel, being adapted to electrically couple said smartcard chip with a mobile communication device, said second data channel coupled to said smartcard chip,
   where said first data channel is different from said second data channel, where said smartcard chip configured to authenticate said mobile communication device before said smartcard chip is enabled to provide data information to a third party terminal.

2. The module of claim 1, further comprising an antenna for communicating wirelessly between said smartcard processor chip and said third party terminal, said antenna coupled to said first data channel.

3. The module of claim 2, further comprising a translation circuit in said second data channel.

4. The module of claim 1, further comprising a housing for encapsulating said smartcard processor, wherein said smartcard processor is at least partially contained by said housing within said mobile communication device.

5. The module of claim 1, further comprising a housing for encapsulating said smartcard chip wherein said smartcard processor chip contained by said housing is separate from said mobile communication device.

6. The module of claim 5, further comprising a fastener system for mechanically coupling said housing to said mobile communication device.

7. The module of claim 1, wherein said smartcard processor chip has a unique identification number.

8. A transaction controller comprising:
   a mobile user interface device; and
   a smartcard chip comprising:
      a data channel, being adapted to wirelessly communicate transaction data between said chip and a third party terminal capable of transceiving smartcard radio signals;
   wherein said mobile user interface device being adapted to transmit user information to said chip, said chip being disposed between said mobile user interface device and said third party terminal,
   where said smartcard chip configured to authenticate said mobile user interface device before said smartcard chip is enabled to provide data information to a third party terminal.

9. A transaction controller as defined in claim 8 wherein where said mobile user interface device configured to authenticate said smartcard chip before said mobile user interface device enables said smartcard chip to provide data information to a third party terminal.

10. A transaction controller as defined in claim 8 wherein said processor is adapted to compare device identification data stored within said processor and device identification data of said mobile user interface device.

11. A transaction controller as defined in claim 8 wherein said mobile user interface device is adapted to compare personal identification data stored within said mobile user interface device with data entered into said mobile user interface.

12. A transaction controller as defined in claim 9 wherein said data channel circuit communicates transaction data with said third party terminal using smartcard compliant communication standards.

13. A transaction controller as defined in claim 9 wherein said user information is stored within said mobile user interface device.

14. A transaction controller as defined in claim 9 wherein said user information is stored with said processor.

15. A transaction controller as defined in claim 9 wherein said mobile user interface device is adapted to be removable coupled to said processor.

16. A transaction controller as defined in claim 9 wherein said mobile user interface device comprises a keyboard.

17. A transaction controller as defined in claim 9 wherein said keyboard comprises a numeric keypad.

18. A transaction controller as defined in claim 9 wherein said mobile user interface device comprises a biometric device.

19. A transaction controller as defined in claim 9 wherein said user information comprises a personal account information.

20. A transaction controller as defined in claim 9 wherein said data channel circuit comprises:
   a radio frequency transmitter; and
   an antenna coupled to said radio frequency transmitter.

21. A transaction controller as defined in claim 9 wherein said mobile user interface device comprises a mobile communicator.

22. A transaction controller as defined in claim 21 wherein said mobile communicator comprises a cellular telephone.

23. A transaction controller as defined in claim 21 wherein said mobile communicator comprises a handheld computer.

24. A smartlink module configured to be coupled to a mobile communication device, comprising:
   an antenna for communicating wirelessly with a third party smartcard transceiving device using smartcard radio frequencies; and
   a smartcard chip for converting radio waves received by said antenna to electrical signals, for converting electrical signals to radio waves and for providing said radio waves to said antenna, said electrical signals being either analog or digital signals, said radiowaves being in the form smartcard radio frequencies, wherein said smartcard chip is configured to be electrically coupled to a mobile communication device, said smartcard chip electrically coupled to said antenna, where before said smartcard chip is enabled to provide data information through radio waves to a third party smartcard transceiving device said smartcard chip is configured to authenticate said mobile communication device.

25. The module of claim 24, wherein said antenna communicates wirelessly using contactless smartcard radio frequencies.

26. The module of claim 24, wherein said smartcard chip is configured to convert data received in a first form from said mobile communication device to data in a second form to be provided to said antennae.

27. The module of claim 25, wherein said smartcard chip further comprises a unique identification code.

28. The module of claim 24, wherein said smartcard chip is configured to compare mobile communication device information received from said mobile communication device to mobile communication device identification information stored in said smartcard chip.

29. The module of claim 28, wherein said smartcard chip is configured to provide data to said antennae depending on said comparison of said mobile communication device information received from said mobile communication device to said mobile communication device identification information stored in said smartcard chip.

30. The module of claim 29, wherein said smartcard chip is configured to store user account information.

31. The module of claim 29, wherein said smartcard chip is configured to receive user account information from said mobile communication device.

* * * * *